(12) United States Patent
Lebovic et al.

(10) Patent No.: US 11,684,146 B2
(45) Date of Patent: Jun. 27, 2023

(54) PERSONAL CLEANSING WAND

(71) Applicant: Silicon Valley Innovations, Inc., Reno, NV (US)

(72) Inventors: Gail S. Lebovic, Reno, NV (US); Michael J. Drews, Palo Alto, CA (US); Steven N. Grolle, Los Altos, CA (US); George D. Hermann, Los Altos Hills, CA (US)

(73) Assignee: Silicon Valley Innovations, Inc., Reno, NV (US)

( * ) Notice: Subject to any disclaimer, the term of this patent is extended or adjusted under 35 U.S.C. 154(b) by 0 days.

(21) Appl. No.: 17/472,478

(22) Filed: Sep. 10, 2021

(65) Prior Publication Data

US 2022/0104611 A1 Apr. 7, 2022

Related U.S. Application Data

(60) Provisional application No. 63/088,141, filed on Oct. 6, 2020.

(51) Int. Cl.
*A46B 15/00* (2006.01)
*A61B 17/24* (2006.01)
(Continued)

(52) U.S. Cl.
CPC .......... *A46B 15/0034* (2013.01); *A01N 33/12* (2013.01); *A61B 17/24* (2013.01);
(Continued)

(58) Field of Classification Search
CPC . A61B 17/24; A61B 2017/246; A61F 11/006; A46B 9/005; A46B 2200/108
See application file for complete search history.

(56) References Cited

U.S. PATENT DOCUMENTS 1,520,908 A 12/1924 Meyer
1,658,801 A  2/1928 Condren
(Continued)

FOREIGN PATENT DOCUMENTS

KR 10-2009-0116067 * 11/2009
KR 10-2014-005010  * 1/2014

OTHER PUBLICATIONS

International Search Report dated Dec. 17, 2021, for PCT Application No. PCT/US2021/049959, filed on Sep. 10, 2021, 3 pages.
(Continued)

*Primary Examiner* — Sarah A Simpson
*Assistant Examiner* — Lindsey Bachman
(74) *Attorney, Agent, or Firm* — Cooley LLP

(57) ABSTRACT

Described herein are devices for cleansing the internal surface of various body cavities. The devices generally include a handle and one or more cleansing tips having different sets of cleansing surfaces. In addition to removing debris, and disrupting bacterial biofilms so as to make these bacteria more susceptible to various cleansing agents, the devices may be configured to deliver an antiseptic agent, an anti-inflammatory agent, or a fragrance to the body cavity surfaces, or deliver UV light to sanitize the surfaces. Methods for cleansing the surfaces of body cavities such as the nasal passages and vaginal cavity are also described herein. Systems including one or more cleansing devices and one or more cleansing formulations are further described.

23 Claims, 29 Drawing Sheets

US 11,684,146 B2
Page 2

(51) Int. Cl.
*A61F 11/00* (2022.01)
*A01N 33/12* (2006.01)
*A61B 17/42* (2006.01)

(52) U.S. Cl.
CPC ...... *A61B 17/42* (2013.01); *A46B 2200/1006* (2013.01); *A61B 2017/246* (2013.01); *A61F 11/006* (2013.01)

(56) References Cited

U.S. PATENT DOCUMENTS

| | | | |
|---|---|---|---|
| 2,096,162 A | | 10/1937 | Daley |
| 3,923,061 A | * | 12/1975 | Rossignol ................ A47K 7/00 600/572 |
| 4,746,238 A | | 5/1988 | Levine |
| 4,935,001 A | | 6/1990 | George |
| 5,715,559 A | | 2/1998 | Mitri |
| 6,358,231 B1 | | 3/2002 | Schindler et al. |
| 7,951,106 B1 | * | 5/2011 | Perez .................... A61F 11/006 604/11 |
| 8,241,236 B2 | | 8/2012 | Yardley |
| 8,999,406 B2 | | 4/2015 | Willimann |
| 9,233,027 B1 | * | 1/2016 | Jackson ................ A61F 11/006 |
| 2005/0240147 A1 | * | 10/2005 | Makower ........... A61B 17/3201 604/96.01 |
| 2008/0142385 A1 | * | 6/2008 | Stein ...................... A61F 13/38 206/362 |
| 2008/0300527 A1 | | 12/2008 | Bivins et al. |
| 2013/0184684 A1 | * | 7/2013 | Yardley ................. A61B 17/24 604/514 |
| 2015/0297846 A1 | * | 10/2015 | Given .................. A61K 31/192 128/200.14 |
| 2016/0135995 A1 | | 5/2016 | Burres |
| 2016/0206869 A1 | | 7/2016 | Burkholz et al. |
| 2019/0209390 A1 | | 7/2019 | Silvaroli |
| 2019/0321228 A1 | * | 10/2019 | Romagnoli ........... A61F 11/006 |
| 2021/0077383 A1 | * | 3/2021 | Reitz ..................... A61K 9/0043 |
| 2021/0386188 A1 | * | 12/2021 | Gillespie .............. A46B 5/0095 |

OTHER PUBLICATIONS

Written Opinion of the International Searching Authority dated Dec. 17, 2021, for PCT Application No. PCT/US2021/049959, filed on Sep. 10, 2021, 8 pages.

\* cited by examiner

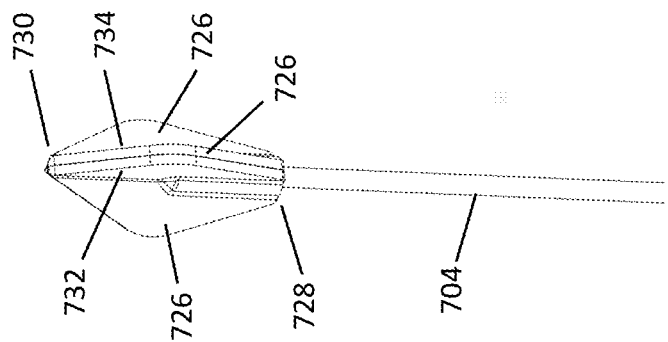
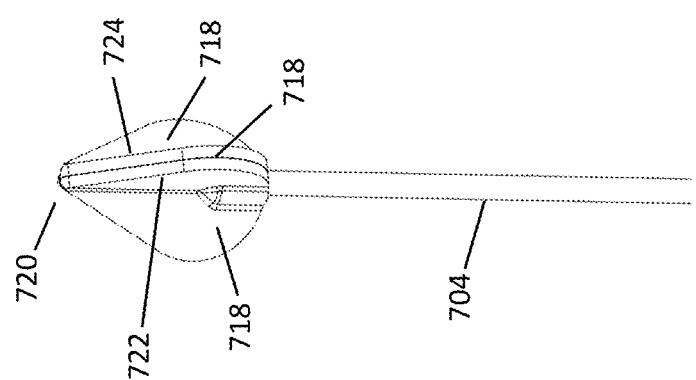
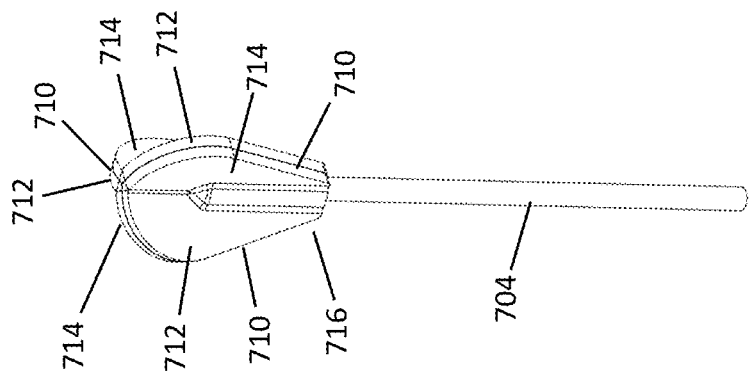

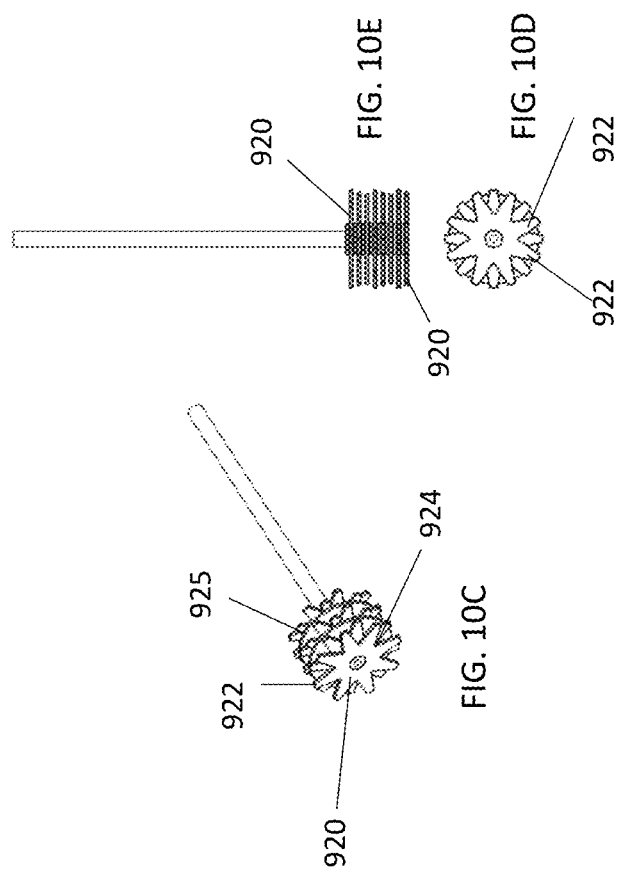
FIG. 10F
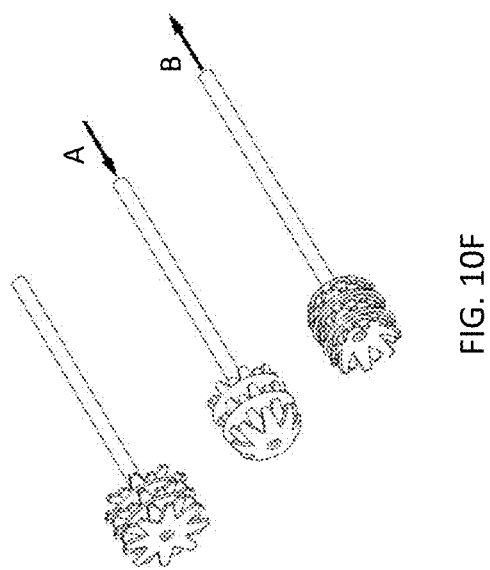
FIG. 10E
FIG. 10D
FIG. 10C

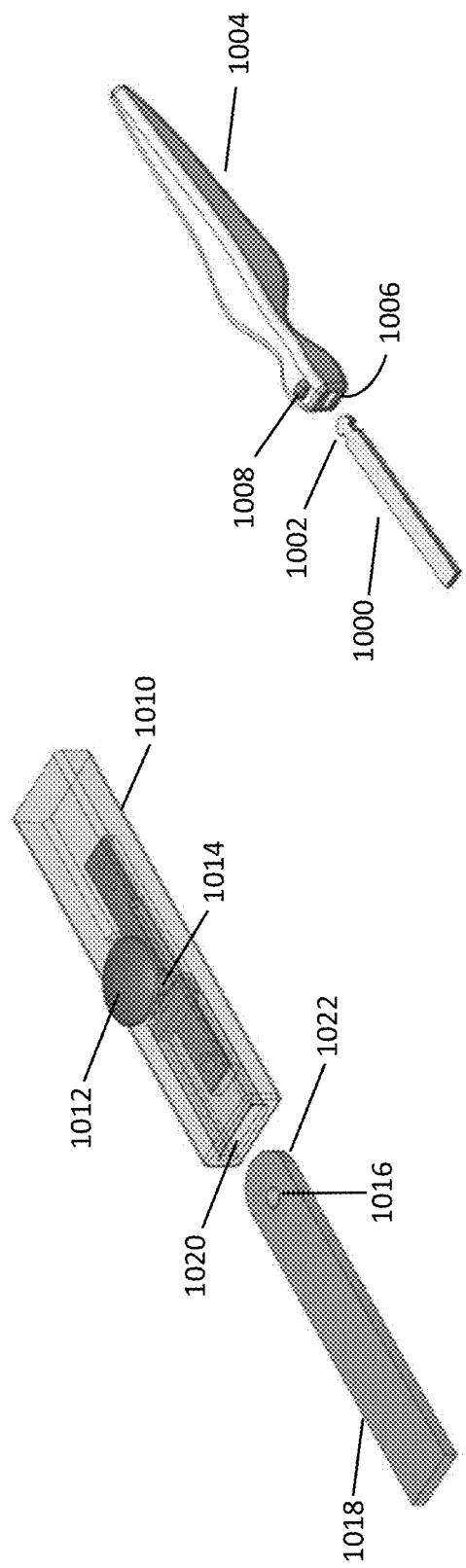

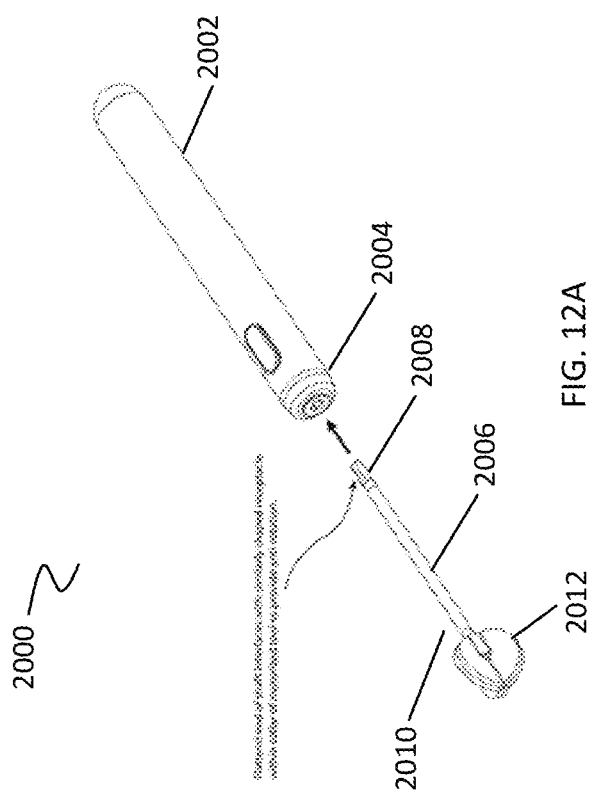

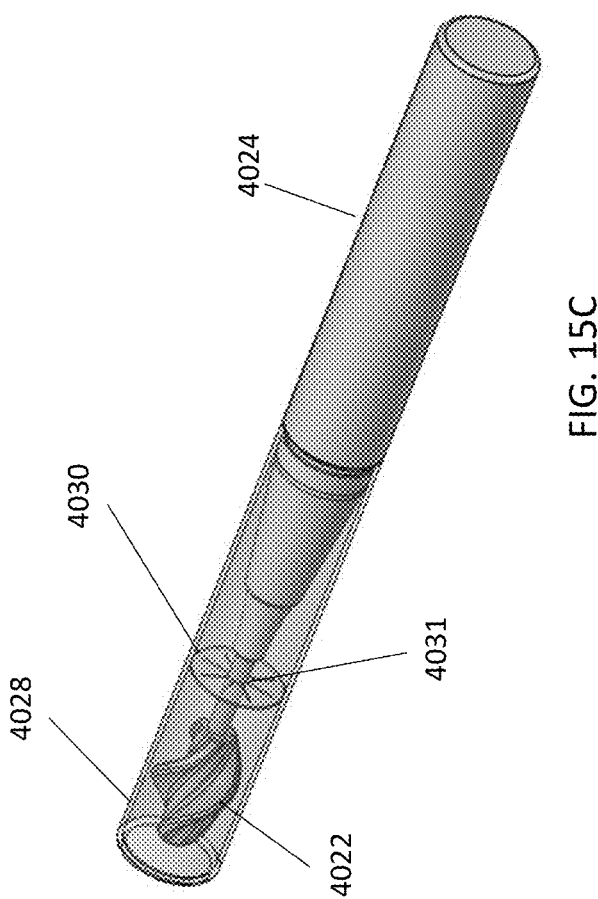
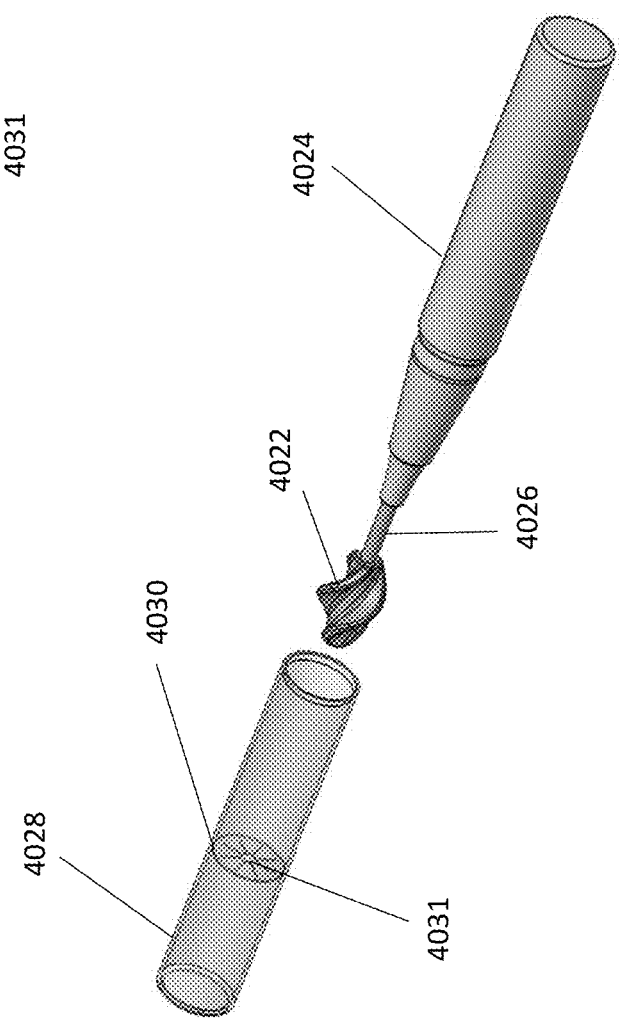
FIG. 15C
FIG. 15D

PERSONAL CLEANSING WAND

CROSS-REFERENCE TO RELATED APPLICATIONS

This application claims priority to U.S. Provisional Application Ser. No. 63/088,141 filed Oct. 6, 2020, which is hereby incorporated by reference in its entirety.

FIELD

This application relates to devices and methods for cleansing the internal surfaces of various body cavities such as the nasal passages and the vaginal cavity. Cleansing is generally achieved using mechanical debridement. The devices may include a handle and one or more cleansing tips having different sets of cleansing surfaces that mechanically remove debris. In addition to debris removal, the devices may be configured to deliver various substances (e.g., antiseptic substances) to the body cavity surfaces, or deliver UV light to sanitize (disinfect) the surfaces. Systems including one or more cleansing devices and one or more cleansing formulations are also described herein.

BACKGROUND

We live in a world that is filled with microbial organisms that are invisible to the eye, but which are ever present in our environment. Some are good, but others can be harmful to humans and/or animals. For example, pathogens such as bacteria, viruses, molds, and fungi are ubiquitous in our surroundings. Additionally, some allergens can enter the human body and initiate inflammatory processes such as rhinitis and sinusitis. Individuals may also react adversely to noxious fumes, smoke, and particulate matter in the air.

Although the skin provides a unique protective barrier on the surface of the body, there are openings or anatomic orifices that provide a point of entry into the body for pathogens, allergens, immunogens, and other substances that can cause health related problems ranging from mild to severe. In some cases, lethal septicemia begins with the entry of pathogens via the nasopharynx or the oropharynx. These orifices include but are not limited to, the mouth, the nose, the eyes, the ears, the female genital tract and the anorectal area.

Most human orifices and cavities are lined with special cells called epithelial cells that interact with pathogens and other substances as a first line of defense. Furthermore, cavities such as the nasal cavity are also lined with tiny hairs called cilia that work to try and prevent entry of pathogens into the human body. While these systems are quite sophisticated, they are limited in their ability to completely eliminate the possibility of infection or inflammation from microbes or allergens. Once a foreign substance or microbe is situated within an anatomic orifice, the human body mounts an immune response that helps us fight off infections. However, the ability of the human body to prevent infection by mounting an immune response is not perfect and success depends upon many factors including the "load" or degree of exposure to a particular pathogen. Viral or bacterial "load" refers to the actual number of organisms with increasing risk of infection occurring in direct correlation to increased "load" or exposure to a specific pathogen.

Thus, external measures are often used to help remove undesirable pathogens or particulates from the body surface, a body orifice, or a body cavity to assist with decreasing their load and to prevent entry into the body. For example, washing or lavage with water or other fluid substances, or the topical application of antiseptic formulations such as those used to clean the skin surface of the hands may be employed. Other barrier-type measures such as gloves, face masks or face coverings may also be used to filter the inhaled ambient air in order to reduce the exposure and transmission of infectious agents or prevent particulate matter from entering the body through the nose and/or the mouth. However, while these measures may be helpful, they may not be effective if, for example, the face covering does not include pores small enough for filtering the pathogens or particulates, if protective barriers are not worn properly, if an insufficient amount of the topical antiseptic is used or the concentration of antiseptic agent such as alcohol is insufficient, or if the washing or lavage is not performed correctly or done for a prolonged period of time.

Additionally, some forms of bacteria, such as methicillin resistant *Staphylococcus aureus*, form cohesive layers that may be difficult to penetrate by antiseptics or antibiotics. These layers, known as "biofilms," may be very significant in clinical practice. Biofilms may allow certain strains of bacteria to behave in a manner that are resistant to normal methods of cleansing, sterilization, decontamination or decolonization. Without disrupting these biofilms or cohesive layers of bacteria, routine methods of cleansing can be rendered ineffective. However, if the surface of the biofilm(s) can be disrupted using a method know as debridement, this can allow penetration of the antiseptic or other cleansing substance(s).

Accordingly, it would be useful to have alternative devices, systems, and methods for removing pathogens, allergens, or other particulate matter from body orifices or the surface of body cavities.

SUMMARY

Described herein are personal cleansing devices and methods for cleansing the surface of a body cavity. In some instances, body cavity surfaces are cleansed by debridement. The devices may include a handle and one or more cleansing tips generally configured to remove debris (e.g., particulate matter) mechanically, via debridement of the body cavity surface. Types of debris that may be removed include without limitation, mucus, dust, pollen, dead skin cells, bacteria, viruses, or combinations thereof. The cleansing tip may include different sets of cleansing surfaces that are exposed depending on how the handle and/or cleansing tip is moved. For example, rotation in opposite directions or axial translation in opposite directions may expose different cleansing surfaces of the tip. The rotation may expose a new clean surface when rotated in the opposite direction after being used to clean in the other direction.

In addition to debridement, the devices may deliver various substances to the body cavity surface. Alternatively, the substances may be provided separately (e.g., packaged separately) and applied to the devices prior to cleansing. The substances may comprise an active agent, for example, an antiseptic agent, to help reduce the bacterial or viral load present on the cavity surface. The antiseptic agent may be formulated such that it creates a film on the cavity surface. This film may provide protection against pathogens for up to several hours. Other substances such as anti-inflammatory agents or fragrances may also be delivered. Systems are also described herein that may include one or more cleansing devices and one or more gel formulations comprising an active agent. In some variations, the systems may include one or more handles and a plurality of cleansing tips that may be attached prior to cleansing or interchanged by the user during cleansing.

The devices for cleansing a surface of a body cavity may include a handle comprising a proximal end and a distal end, and a cleansing tip coupled to the distal end. The cleansing tip may include a plurality of cleansing surfaces (e.g., "leaflets") that comprise a first set of cleansing surfaces and a second set of cleansing surfaces. Upon movement of the cleansing tip in a first direction, the first set of cleansing surfaces may remove debris from the body cavity surface. When the cleansing tip is moved in a second opposite direction, the second set of cleansing surfaces may be exposed to further remove debris. The first direction and the second opposite direction may be rotation, for example, the first direction may be clockwise rotation, and the second opposite direction may be counterclockwise rotation. Alternatively, the first direction and second opposite direction may be axial translation. For example, the first direction may be linear advancement of the cleansing tip into the body cavity, and the second opposite direction may be linear withdrawal of the cleansing tip out of the body cavity.

The cleansing tip may be directly coupled to the distal end of the handle. Alternatively, depending upon the specific configuration, there may also be a handle that contains a tip at each (both) ends. However, in some instances the device includes a shaft having a proximal end and a distal end, where the shaft proximal end may be coupled to the distal end of the handle, and the shaft distal end may be coupled to a cleansing tip. The cleansing tip may be fixed to the distal end of the shaft or attachable using various designs, or slidable over the distal end of the shaft. In some instances, the shaft may be rigid. In other instances, the shaft may be malleable or substantially flexible. With respect to the handle, it may also be fixed to the proximal end of the shaft or removably coupled to the proximal end of the shaft. The handle may be removably coupled to the shaft via friction fit between the components, a threaded connection, a snap on fit, or via one or more connector pieces, for example, male-female connectors or other complementary shaped fittings. A locking mechanism may also be provided on the handle to secure it to the shaft. The locking mechanism may be helpful when the device is used to cleanse the body cavity in order to ensure the tip does not become dislodged during the cleansing process. The handle and the tip may be reusable or disposable.

The plurality of cleansing surfaces of the cleansing tip are generally sufficiently rigid to allow debridement, but flexible enough so that different sets of cleansing surfaces may be exposed upon movement of the tip in opposing directions, for example, clockwise and counterclockwise rotation, or translation back and forth along a linear axis. The type of material employed to make the cleansing surfaces and/or thickness of material used to make the cleansing surfaces may be adjusted to achieve the desired amount of flexibility and rigidity. More specifically, the amount of flexibility may be adjusted by varying a combination of factors, e.g., by varying the geometry, size, and/or shape of the cleansing surfaces, and by varying the thickness and/or stiffness of the material used to make the cleansing surfaces. The material(s) could have a variable stiffness due to overmolding, overlaying, dipping, injection molding or coextrusion of two or more materials of differing stiffness. Also, the thickness of the plurality of cleansing surfaces could be uniform, non-uniform, or highly variable to modify the apparent rigidity of the geometry. Flexibility of the cleansing surfaces may also be adjusted so that they conform to the shape of the body cavity. The shape of the cleansing surfaces may be varied so as to conform to the variety of shapes and sizes of the surface of the body cavity and debride the surface of the body cavity. The materials used to create the tips may include but are not limited to natural materials such as cotton, wool, or synthetic materials such as polyester, acrylic, silicone or various pliable rubbers, thermoplastic elastomers or a combination thereof. The material would allow for deformation when the tip is inserted into the cavity for comfort, yet it would need to maintain its shape in order to provide some degree of rigidity in order to provide debridement of items from the body surfaces.

The plurality of cleansing surfaces may be variously disposed about the axis of the handle. For example, the plurality of cleansing surfaces may be disposed in a direction parallel to the axis of the handle. They may also be arranged in a spiral or helical pattern about the axis. These orientations may be beneficial when the device is used to cleanse the nasal cavity. Alternatively, the plurality of cleansing surfaces may be disposed in a direction perpendicular to the axis of the handle. The perpendicular orientation may be beneficial when the device is used to cleanse a deeper orifice such as the vaginal cavity. Additionally, the cleansing surfaces may be variously spaced about the cleansing tip. For example, the plurality of cleansing surfaces may be equally spaced apart about the cleansing tip or unequally spaced apart about the cleansing tip.

Some variations of the cleansing tip include a plurality of leaflets, where the cleansing surfaces are surfaces of the leaflets. For example, the first set of cleansing surfaces may be on a first side of the plurality of leaflets, and the second set of cleansing surfaces may be on a second side of the plurality of leaflets. The leaflets may have a proximal end and a distal end. The leaflets may be shaped so that the proximal end may be tapered, the distal end may be tapered, or both the proximal and distal ends are tapered. Furthermore, the plurality of leaflets may have a conical, round, oval, rectangular, hexagonal or triangular shape. The leaflets may be variously disposed about the axis of the handle. For example, the leaflets may be disposed in a direction parallel to the axis of the handle. They may also be arranged in a spiral or helical pattern about the handle axis. These orientations may be beneficial when the device is used to cleanse the nasal cavity. Alternatively, the plurality of leaflets may be disposed in a direction perpendicular to the axis of the handle. The perpendicular orientation may be beneficial when the device is used to cleanse a deeper orifice such as the vaginal cavity.

To increase the amount of debridement, each leaflet of the plurality of leaflets may include one or more separations ("cuts") that divide the leaflet into portions. Any number of separations may be employed to create the desired number of leaflet portions. Each leaflet may have separations that are the same length or different lengths. The separations or cuts may also be made at various angles with respect to the axis of the handle. For example, the separation or cut may form a 45 degree, a 60 degree, or a 90 degree angle with the axis of the handle. Alternatively, devices that increase the amount of debridement may include leaflets having a sharp, cutting edge. The cutting edge may be formed by one or more blades on the leaflet. In some variations, the cutting edge may comprise a serrated edge. When a blade is provided on the leaflet, the cleansing tip may also function as a shaver to remove hair within the nasal cavity.

The plurality of leaflets may include any suitable number of leaflets. For example, the plurality of leaflets may include two, three, four, five, or six leaflets. It may be useful for the cleansing tip to include three leaflets.

Similar to the handle, the cleansing tip may be reusable or disposable. The cleansing tip may be made from various materials such as polymer materials or natural materials. Exemplary polymer materials include without limitation, foam, polyamides, polyesters, rubber, nylon, polypropylene, silicone, thermoplastic elastomers, or combinations thereof. Hardness of the materials may range between about 10 to 80 Shore A durometer values are typical depending on section thickness of the cleansing tips, and other factors. Exemplary natural materials include without limitation, bamboo, cotton, linen, wool, or a combination thereof.

The devices described herein may further include a cartridge for the delivery of various substances. The cartridge may be a reservoir that is replaceable within the device handle, or provided as an integral component within the handle. Alternatively, the cartridge may be a component of a cover that fits over the distal end (tip end) of the device. The cartridge containing various classes of substances may release one or more substances onto the cleansing leaflets of the cleansing tip. Exemplary classes of substances contained within the cartridge include, but are not limited to, antiseptic agents, anti-inflammatory agents, anti-allergy agents, fragrances, or combinations thereof. The antiseptic agents may include antibacterial agents, antiviral agents, or combinations thereof. In some variations, it may be useful to include colloidal silver as the antibacterial or antiviral agent.

The device may also include a source of UV light to help sanitize the surface of the body cavity and reduce the load or number of pathogens (e.g., bacteria, viruses, mold, fungi) thereon. The source will typically be a UV-C light source that emits UV light at a wavelength in the range of about 200 nm to about 280 nm. Here an optical fiber may be coupled to the UV-C light source in the handle and extend through the interior of the shaft of the device up to the distal end of the cleansing tip. The shaft may be provided with openings in its wall for transmission of the UV-C light therethrough to the body cavity surface. The openings may be disposed in various ways on the shaft. For example, the openings may be provided on the entirety of the shaft, either evenly or unevenly spaced apart on the shaft, or they may be disposed on certain portions of the shaft, or they may form a pattern on the shaft.

The entire handle may be rotated manually to rotate the cleansing tip. However, in some instances the handle may include a portion thereof that may be used to rotate the tip, or a motor may be contained within the handle and configured to rotate the cleansing tip about the handle. The motor may be battery powered. A microprocessor and associated circuitry may also be included to adjust the speed of rotation. For example, a switch may be provided on the handle to effect slower rotation or faster rotation of the cleansing tip. Alternatively, the cleansing tip can be rotated by a mechanical mechanism within the handle that is manually actuated by a finger(s), hand(s) or other physical motion by the user. The manual actuation can be accomplished by means of slider, rotating knob, lever, trigger, or other similar feature.

The devices described herein may be used to clean various body cavity surfaces, but will typically be used to cleanse the internal surface of the nasal cavity (nostrils). The nasal cavity may include the skin and hair region of the nostrils. In some instances, and with a different configuration, the devices may be used to cleanse the vaginal cavity. Types of debris removed by the devices include without limitation, mucus, dust, pollen, dead skin cells, bacteria, viruses, and combinations thereof.

Some devices for cleansing a surface of a nasal cavity may specifically include a handle comprising a distal end, and a cleansing tip coupled to the distal end. The cleansing tip may include a plurality of leaflets, where the plurality of leaflets may comprise a first set of cleansing surfaces and a second set of cleansing surfaces. The first set of cleansing surfaces may remove debris from the nasal cavity surface upon rotation of the cleansing tip a first direction, and the second set of cleansing surfaces may remove debris from the nasal cavity surface upon rotation of the cleansing tip in a second opposite direction. The plurality of leaflets may include different numbers of leaflets depending upon the specific body cavity surface to be cleansed. For example, three leaflets that are disposed in a direction parallel to the axis of the handle may be employed when cleansing the nasal cavity. When the device is used in the vaginal cavity, a greater number of leaflets may be used, e.g., four, five, six, seven, or eight leaflets may be included on the cleansing tip and disposed perpendicular to the axis of the handle. The leaflets in all variations described herein may have a contiguous surface area, or they may have perforations, textured surfaces, dimples, ridges, bristles, or one or more discontiguous areas such as slits that create further individual leaflets that are smaller in size.

Devices for cleansing a surface of a vaginal cavity may specifically include a handle comprising a distal end, and a cleansing tip coupled to the distal end. The cleansing tip may include a plurality of leaflets, where the plurality of leaflets are configured in a manner that may comprise a first set of cleansing surfaces and a second set of cleansing surfaces. The first set of cleansing surfaces may remove debris from the vaginal cavity surface upon axial translation of the cleansing tip a first direction, and the second set of cleansing surfaces may remove debris from the vaginal cavity surface upon axial translation of the cleansing tip in a second opposite direction. Here the plurality of leaflets may be disposed in a direction perpendicular to the axis of the handle. In this variation, it may be beneficial for a locking mechanism to be provided for securing the handle to the shaft or the tip. The locking mechanism may be an integral component of the shaft and/or tip, or a separate component.

Systems for cleansing a surface of a body cavity are also described herein and may include one or more handles and a plurality of cleansing tips. At least one of the plurality of cleansing tips may include a plurality of leaflets. Other cleansing tips included with the system may have a different configuration. When a plurality of leaflets are employed, they may include a first set of cleansing surfaces and a second set of cleansing surfaces. The first set of cleansing surfaces may remove debris from the body cavity surface upon movement of the cleansing tip a first direction, and the second set of cleansing surfaces may remove debris from the body cavity surface upon movement of the cleansing tip in a second opposite direction, as previously stated. The first direction and the second opposite direction may be rotation, for example, clockwise and counterclockwise rotation, respectively. Alternatively, the first direction and the second opposite direction may be axial translation, for example, back and forth movement into and out of a body cavity. The handles included with the system may be disposable or reusable. The plurality of cleansing tips are generally disposable, but may be configured to be reusable.

Other systems for cleansing body surfaces may include one or more cleansing devices and one or more gel formulations incorporating an active agent. The one or more cleansing devices may include a cleansing tip, where the cleansing tip comprises a plurality of leaflets, and where each of the plurality of leaflets comprises a first set of cleansing surfaces and a second set of cleansing surfaces, and where the first set of cleansing surfaces removes debris from the body cavity surface upon movement of the cleansing tip in a first direction, and the second set of cleansing surfaces removes debris from the body cavity surface upon movement of the cleansing tip in a second opposite direction. The surface of various body cavities may be cleansed. For example, the body cavity may be the nasal cavity or the vaginal cavity. The gel formulation(s) and type of cleansing tip(s) included in the system may be tailored to the specific anatomy being cleansed or the particular indication for use. For example, an antiseptic gel may be included when the system is to be used to treat or prevent bacterial or viral growth in the nasal cavities. In one variation, the antiseptic gel comprises benzalkonium chloride. The gel formulation of the systems may be dispensed from the handle of the cleansing device or provided in a separate package or packet. The gel may be dispensed from the handle or applied to the cleansing tip at any time during the cleansing process. When provided separately, the gel may be applied to the cleansing tip just prior to insertion of the tip into a body cavity.

Methods for cleansing a surface of a body cavity including, for example a mucosal surface of a body orifice, are further described herein. In general, the methods may include inserting a cleansing device into the body cavity, where the cleansing device may comprise a handle and a cleansing tip, and the cleansing tip may comprise a first set of cleansing surfaces and a second set of cleansing surfaces. Next, the cleansing tip may be moved in a first direction to remove debris from the surface of the body cavity. Thereafter, the cleansing tip may be moved and in a second opposite direction to further remove debris from the surface of the body cavity. Here, moving the cleansing tip from the first direction to the second opposite direction switches the first set of cleansing surfaces to the second set of cleansing surfaces. In addition, the method may include replacing a used cleansing tip with a new, unused cleansing tip.

The cleansing tip may be rotated or axially translated to switch the cleansing surfaces from the first set to the second set. As previously described, the cleansing tip may be rotated in a first direction (e.g., clockwise) to cleanse the surface of a body cavity with the first set of cleansing surfaces, and then rotated in a second opposite direction (e.g., counterclockwise) to further cleanse the body cavity surface with the second set of cleansing surfaces. Similarly, the cleansing tip may be axially translated in a first direction (e.g., advanced into a body cavity) to cleanse the surface of a body cavity with the first of cleansing surfaces, and then axially translated in a second opposite direction (e.g., withdrawn from the body cavity) to further cleanse the surface of the body cavity with the second set of cleansing surfaces.

Movement of the cleansing tip may be manual, for example, by rotating or axially translating the handle of the device by hand. Alternatively, movement of the cleansing tip may be automated, for example, via actuation by a motor housed within the handle. In some variations, the cleansing tip may be rotated by a mechanical mechanism within the handle that is manually actuated by a finger(s), hand(s) or other physical motion by the user. The manual actuation may be accomplished by means of slider, rotating knob, lever, trigger, or other similar feature.

Various body cavity surfaces may be debrided with the cleansing devices described herein. For example, surfaces of the nasal cavity, the oral cavity, the ear canal, or the vaginal cavity may be debrided. Particulates or debris that may be removed include without limitation, mucus, dust, pollen, dead skin cells, bacteria, viruses, and combinations thereof. Given that particulates or debris are being captured and removed by the cleansing tips, they may also be used as swabs for collecting samples. The samples may be collected for bacterial or viral cultures or for DNA analysis of cells. Other uses for the samples are also contemplated.

In addition to debridement, the devices may also deliver a substance (such as a cleansing agent or therapeutic agent) to the surface of the body cavity. Exemplary classes of substances that may be delivered include, but are not limited to, antiseptic agents, anti-inflammatory agents, anti-allergy agents, fragrances, or combinations thereof. The antiseptic agents may include antibacterial agents, antiviral agents, or combinations thereof. The substance may be delivered prior to debridement, during debridement, and/or after debridement.

Additionally or alternatively, the device may emit UV light to help sanitize the surface of the body cavity and reduce the load or number of pathogens (e.g., bacteria, viruses, mold, fungi) thereon. The source will typically be a UV-C light source that emits UV light at a wavelength in the range of about 200 nm to about 280 nm.

BRIEF DESCRIPTION OF THE DRAWINGS

In FIG. 2A, the cleansing tip has an elliptical shape; and in FIGS. 2B and 2C, the cleansing tip has an oval shape.

In FIGS. 5A and 5B the cleansing tip includes twisted material; in FIG. 5C, the cleansing tip includes helically wound filaments; and in FIG. 5D, the cleansing tip includes braided filaments.

In FIG. 6A, the tip includes a plurality of grooves or channels running longitudinally along the tip surface; in FIG. 6B, the tip includes a plurality of grooves or channels extending diagonally along the tip surface; and in FIG. 6C, a single helically winding groove or channel is shown in the tip.

In FIG. 7A, the cleansing tip has an umbrella shape; in FIG. 7B, the cleansing tip has a circular shape and includes a plurality of leaflets; and in FIG. 7C, the cleansing tip includes a plurality of leaflets tapered at both the proximal and distal ends.

FIGS. 10A-10F depict exemplary devices for debridement of the surface of the vaginal cavity.

FIGS. 11A and 11B depict exemplary handles and mechanisms for coupling to a shaft of the device.

FIGS. 12A-12C illustrate motorized rotation of the cleansing tip with respect to the handle.

FIGS. 15A-15D depict exemplary devices that debrides a body cavity surface as well as deliver a substance to the surface via the cleansing tip.

In FIG. 19A, the leaflets are disposed parallel to the axis of the handle. In FIG. 19B, the leaflets are disposed in a helical manner about the axis of the handle.

DETAILED DESCRIPTION

Figure 2C:
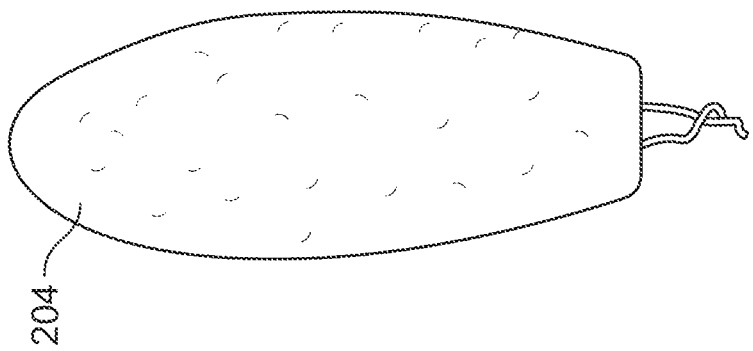
FIGS. 2A-2C depict other exemplary cleansing tips having various shapes.

Described herein are personal cleansing devices and methods for cleansing the surface of a body cavity. The devices may include a handle and a cleansing tip generally configured to remove debris mechanically, via debridement of the body cavity surface. The devices may include one cleansing tip at the distal end of the handle, or two cleansing tips, one at each end of the handle. The types of debris that may be removed include without limitation, mucus, dust, pollen, dead skin cells, bacteria, bacterial biofilms, viruses, or combinations thereof.

The cleansing tip may include different sets of cleansing surfaces that are exposed depending on how the handle and/or cleansing tip is moved. For example, rotation in opposite directions or axial translation in opposite directions may expose different cleansing surfaces. The cleansing surfaces may be leaflets with one or more characteristics that may result in improved cleansing of the interior surface of body cavities. For example, the number of leaflets employed may be beneficial in improving the effectiveness of cleansing over swabs having smooth surfaces. Cleansing tips including two or more leaflets may generally have improved cleansing ability compared to a swab having a single smooth surface. Additionally, increasing the number of leaflets provides additional surface area for cleansing. When texturing is used on the leaflets, the texturing may provide further additional surface area for cleansing as well as providing enhanced debridement capability. These same enhanced features for debridement may lend the device to be particularly useful in collecting samples and should increase the sample yield compared to using a swab. In addition to debridement, the devices may deliver an antiseptic agent to help reduce the bacterial or viral load present on the cavity surface. Other substances such as anti-inflammatory agents or fragrances may also be delivered. Systems are also described herein that include one or more handles and a plurality of cleansing tips. The handles may be disposable or reusable. The cleansing tips will typically be disposable. However, in some variations they may be reusable and made from materials capable of being sterilized or disinfected, e.g., by washing, soaking or wiping with ethyl alcohol or another disinfecting agent.

The devices may be employed to debride the surface of various body cavities. For example, surfaces of the nasal cavity, the oral cavity, the ear canal, or the vaginal cavity, the entry region of the vaginal canal, or other potential spaces, including those with mucosal surfaces, may be debrided. The nasal cavity is an exemplary area for entry of particulate matter that can be infectious, allergenic, or toxic. If there is particulate matter, it may become lodged in the nasal cavity opening and ultimately may be transferred deeper into the sinus cavities or respiratory track leading to infection and creating the possibility for contagious transfer of bacteria, viruses, mold, etc.

Another exemplary area for debridement may be the female genital tract where the vaginal cavity provides a means by which menstrual flow exits the body each month and through which childbirth occurs. The same cavity provides a potential entry point for pathogens and sexually transmitted diseases via intercourse. The vaginal cavity is in direct continuity with the uterine opening, which provides a direct means of entry via the fallopian tubes into the abdominal cavity. It is in this manner that pelvic inflammatory disease (PID) is transmitted and can cause severe disease, sterility, and even death.

The anatomy of the vaginal cavity (canal) allows for a tremendous amount of expansion with the ability to markedly increase the diameter of the cavity such that it can accommodate childbearing. This is possible due to the laxity of the tissues within and supporting the cavity (canal). In the relaxed or collapsed state, there are numerous folds within the lining of the cavity, making it very challenging for cleansing simply with lavage (douching) or with application of fluids or gels. With each menstrual cycle, particulate matter including small blood clots shed from the uterine lining and may become entrapped in the many folds of the vaginal cavity and these can serve as a nidus for infection leading to an increased risk of PID or other diseases. The devices described herein may be able to gently expand the vaginal cavity to smooth out the cavity surface such that the folds and crevices may be more easily debrided to remove particulate matter or infectious agents. Furthermore, the leaflets of the cleansing tips attached to the device may provide additional surface area for cleansing in the vaginal canal using mechanical debridement. If texturing is also included on the leaflets, additional surface area for cleansing and mechanical debridement may also be provided.

In some variations, the cleansing devices may include a sharp or cutting edge. The sharp or cutting edge may increase the amount of debridement of the body cavity surface. Sharp or cutting edges may be formed by one or more blades provided on the leaflet. Alternatively, the sharp or cutting edge may comprise a serrated edge. When a blade is provided on the leaflet, the cleansing tip may also function as a shaver to remove hair within the nasal cavity.

In some variations, the cleansing devices described herein may be used as a diagnostic tool. Given that particulates or debris are being captured and removed by the cleansing tips, they may also be used for sample collection. The samples may be collected for bacterial or viral cultures in the case of needing diagnostic information or therapeutic intervention. In the case of analysis in the legal setting for DNA analysis (such as following a rape), the ability to obtain a larger sample of DNA from the vaginal canal may prove to be beneficial.

In other variations, the size and shape of the cleansing tips may not be size-matched to the anatomic cavity for which it will be used. For example, the cleansing tip may be undersized to the nostril region, and the nostril region cleansed as the tip and/or leaflets move (e.g., rotate) freely within it. A varying amount of force may be applied to the various anatomic cavities and cavity surfaces to provide appropriate cleansing or debridement in a comfortable manner. The leaflets may also be designed with a flexibility and/or resiliency that allows them to conform to the anatomic shape of various body cavities. Additionally, the shape and size of the cleansing tips and leaflets may be configured to be self-limiting within the particular anatomic cavity. For example, the curvature of the cleansing tips (e.g., the helical or spiral shaped tips) may limit its depth of penetration so as to protect the user from entering the sinus cavity.

In further variations, a substance is used with the cleansing devices. The substance may be included in a gel, foam, or other substrate or carrier. The gel may be applied to the tip of the cleansing device to provide lubrication so that the cleansing device may be comfortably inserted into a body cavity. The leaflets may also be configured to deform in order to comfortably allow insertion into the body cavity. Movement of the leaflets may allow cleansing or debridement simultaneously with distribution of the gel on the body cavity surface. When used in the nose, the cleansing device may provide cleansing of the skin and hair inside the nose. The viscosity of the gel may be generated to have a target dwell time that improves antiseptic efficacy (e.g., to allow sufficient kill time), or a target dwell time that improves the longevity of substances (e.g., the anti-inflammatory effect of substances). In one variation, a target dwell time may be achieved with a gel formulation having a viscosity of about 7,520 cP (about 7.5 Pa-s). Gels in the range of about 500 cP (about 0.5 Pa-s) to about 15,000 cP (about 15 Pa-s) may be appropriate depending upon the given anatomic location or desired effect. In other situations, a foam may potentially be used with the cleansing devices in a similar manner as the gel.

Devices

Handle and Shaft

The devices for cleansing a surface of a body cavity generally include an elongate handle comprising a distal end, and one or more cleansing tips coupled thereto. The one or more cleansing tips may be coupled to the distal end of the handle or the both the distal and proximal ends of the handle. When more than one cleansing tip is employed, the tips may be made from the same or different materials. For example, a first tip may be made from an elastomer while the second tip is made from cotton. The tips may also have the same configuration or different configurations. For example, a first tip may include leaflets disposed in a spiral fashion about the handle while the second tip may include leaflets disposed parallel to the axis of the handle.

The handle may be straight with rounded edges or features for gripping. Other variations of the handle may include various ergonomic features. For example, the handle may include a grip portion, for example, a shaped or textured area that is easily grasped by a user. The handle may also include features that prevent slippage when the handle is rotated or moved in a forward/backward motion within a cavity such as the vaginal canal. Additionally, the handle may include a freely rotating portion at the handle base to facilitate rotation of the handle via the fingers while still maintaining stability and support of the base (e.g. against the user's palm). The handle may also include a thumb or other finger rest to enhance comfort and hold on the device. In some variations, the handle is a paper stick. In one variation, the cleansing device may include a paper stick having a cleansing tip at its distal end. In another variation, the cleansing device may include a paper stick having two cleansing tips, one at the proximal end of the stick, and one at the distal end of the stick. The paper stick may comprise rolled paper or compressed paper.

Figure 15A:
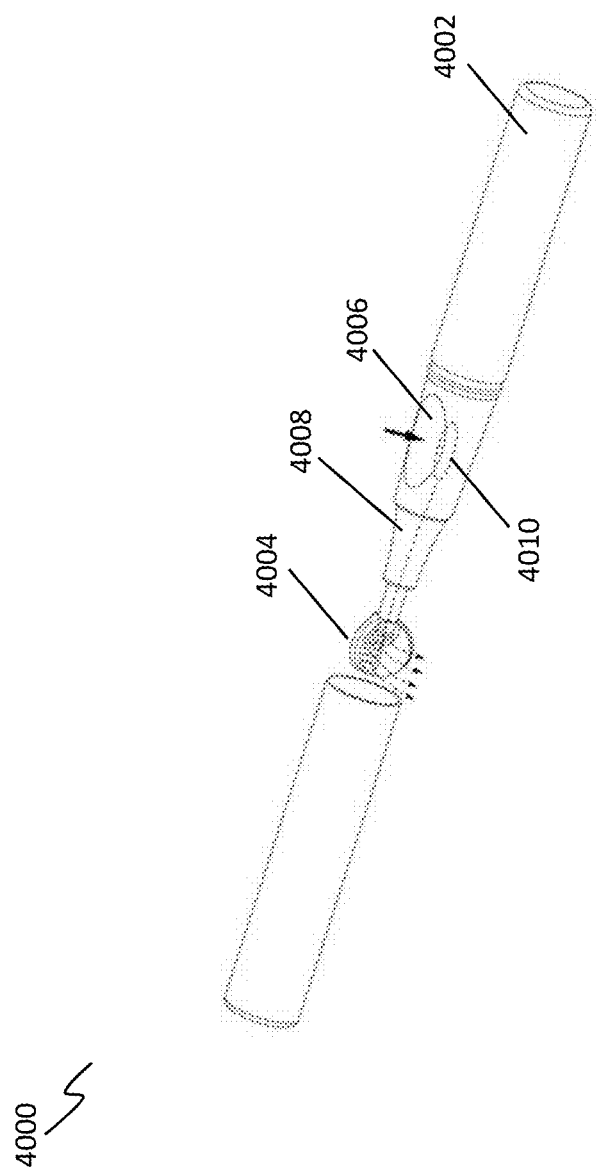
Figure 15B:
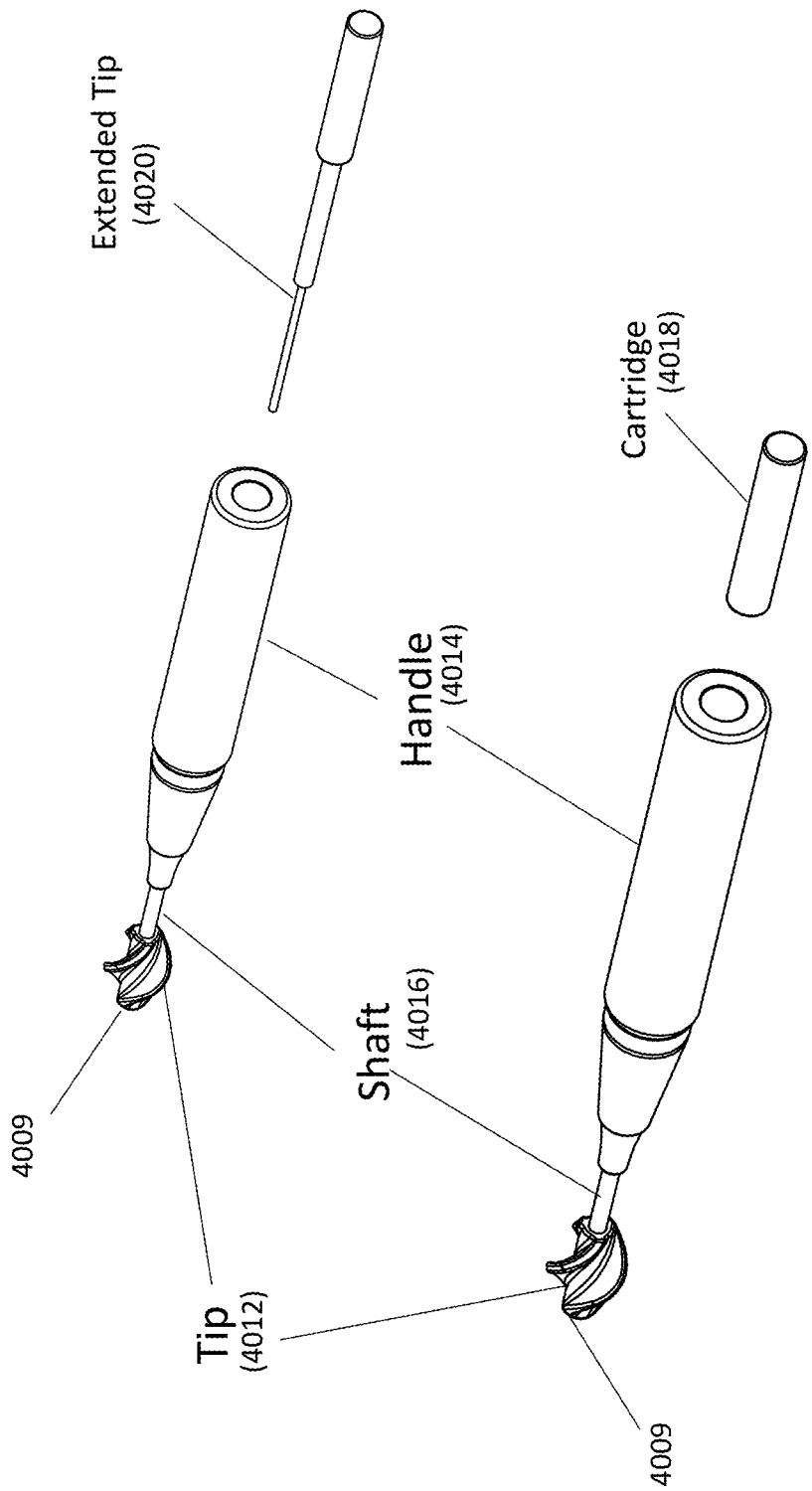

In some variations, the handle may include one or more features for dispensing substances or activating the UV light source. For example, a push button or switch may be included to actuate substance delivery or turn on the UV light. Referring to FIG. 15A, an exemplary debridement device (4000) is shown including a handle (4002) and a cleansing tip (4004). A push button (4006) on the handle (4002) may be depressed in the direction of the arrow to deploy a substance contained within a cartridge or reservoir (4010) through tubing (4008) and out onto the leaflets of the cleansing tip (4004). The reservoir or cartridge may be compressible such that depression of push button (4006) compresses the reservoir or cartridge (4010) and pressurizes it so that the substance flows from the reservoir or cartridge (4010) and out of the cleansing tip (4004) onto a body cavity surface. In another variation, as shown in FIG. 15B, the debridement device may include a cleansing tip (4012) coupled to a handle (4014) via a shaft (4016). A cartridge (4018) containing a substance (e.g., a substance in a liquid or gel carrier) may be disposed within handle (4014). The substance cartridge may be replaceable or refillable. Cartridge (4018) may include an extended tip (4020) that travels through the handle (4014) to connect the cartridge to the cleansing tip (4102) such that the substance may flow or be delivered to the cleansing tip (4012) and out onto the leaflets. The substance may flow out of, or be delivered through, the distal tip (4009) of the cleansing tip, or delivered via openings (not shown) spaced upon the cleansing tip, and onto a cavity surface. In yet a further variation, as shown in FIGS. 15C and 15D, the debridement device may also include a cleansing tip (4022) coupled to a handle (4024) by a shaft (4026). However, in this variation, the device includes a cap (4028) comprising a substance, which is contained within the cap (4028) by a diaphragm (4030). When the cap (4028) is placed on the cleansing tip (4022), as shown in FIG. 15C, the tip (4022) is advanced through opening (4031) in the diaphragm (4030) and immersed within the substance contained in the cap (4024). Upon removal of the cap (4024), as shown in FIG. 15D, the substance will be coated on the leaflets of the cleansing tip (4022).

The handle may be provided in various lengths depending on such factors as the age of the user, the type of cleansing tip being employed, and the body cavity or anatomical region being debrided. The length of the handle may range from about 4 cm to about 20 cm, including all values and sub-ranges in between. For example, handle length may be about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm.

The handle may be made from various materials. For example, the handle may be formed from plastic components such as styrene, acrylonitrile butadiene styrene (ABS), nylon, a polyolefin, glass, plant-based plastics, or combinations thereof. The handle may also be formed from a metal, a rubber material, compressed paper material, rolled paper material, wood, bamboo, other natural or synthetic materials, or combinations thereof. The handle may be configured such that it allows the user to grasp the device without touching the tip(s) so that they may in some cases be provided sterile. The handle also allows the user to rotate or move the device longitudinally without contaminating the tip(s).

As further described below, the handle may house a cartridge or reservoir containing a substance for delivery to the body cavity surface. If a UV light source is included, it may also be provided in the handle. Additionally, any power source for the UV light or motorized movement of the cleansing tip may be disposed within the handle. The motor may be battery powered. A microprocessor and associated circuitry may also be included to adjust the speed of rotation. For example, a switch may be provided on the handle to effect slower rotation or faster rotation of the cleansing tip. In some variations, the handle may be rotated manually to rotate to the cleansing tip.

Figure 10B:
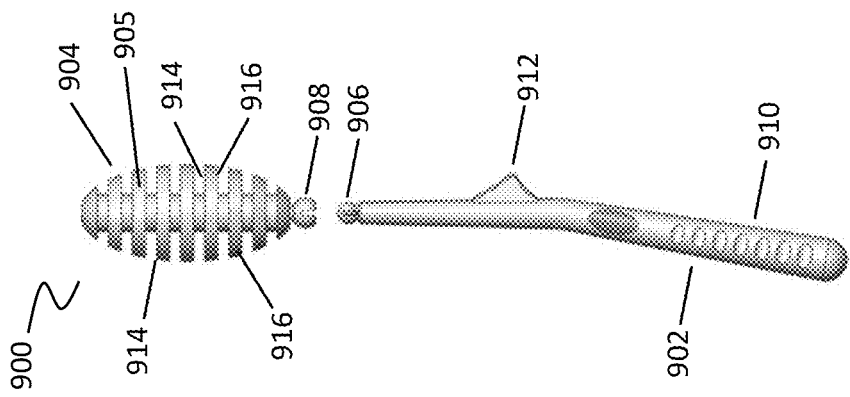

The cleansing tip may be directly coupled to the distal end of the handle. For example, referring to FIGS. 13A and 13B, debridement device (3000) includes a handle (3002) having a proximal end (3004), a distal end (3006), a grip portion (3016), and a thumb rest (3014). At the distal end (3006) of handle (3002), a male connector (3008) may be provided that is capable of quickly mating with a corresponding female connector (3010) on the cleansing tip (3012). This type of quick connection may be useful for the systems described in further detail below. Other types of connectors may be used to couple the cleansing tip to the handle. For example, ball and socket type joints may be employed, as shown in FIG. 10B. This type of connection allows a straightforward mechanism for a "no touch" technique allowing the tip to be used and disposed of without contaminating surrounding surfaces if a pathogen has been cleared from the anatomical region being cleansed. Similarly, the "no touch" technique allows for delivery of substances that potentially may need to be introduced into a body cavity in a sterile or clinically "clean" manner.

Figure 16B:
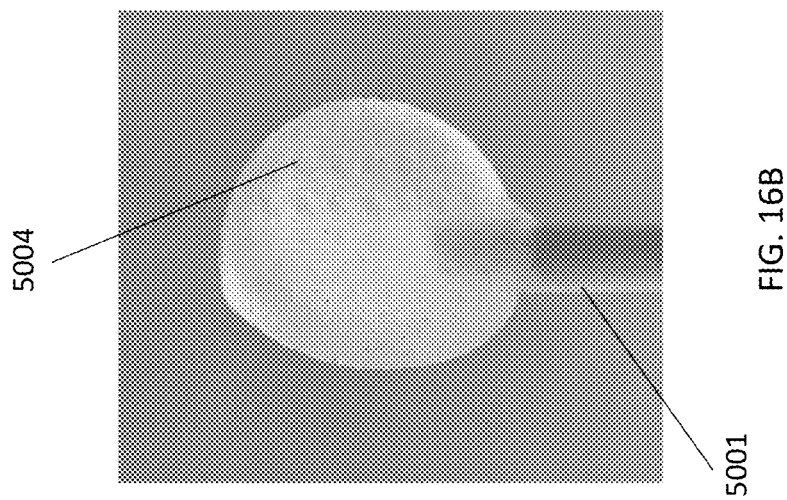
FIGS. 16A-16C depict exemplary polymeric cleansing tips.

The cleansing tip may also be provided to users pre-attached to the handle. A single cleansing tip or multiple cleansing tips may be provided pre-attached. For example, referring to FIGS. 16A and 16B, a single cleansing tip (5000, 5002) may be pre-attached to handle (5001). The tips may be molded onto the handle, fixed to the handle by adhesive, or attached to the handle by sliding the tip over the distal end of the handle. Although the tips shown in FIGS. 16A and 16B include leaflets that spiral about the handle axis or are parallel to the handle axis, it is understood that the cleansing tips may have any configuration described herein. When multiple cleansing tips are provided pre-attached to the handle, the devices may be configured as shown in FIG. 17. Referring to FIG. 17, cleansing device (6000) includes a handle (6002) having a first end (6004) and a second end (6006), and two cleansing tips, a first cleansing tip (6008) pre-attached to the first end (6004) and a second cleansing tip (6010) pre-attached to the second end (6006).

However, in some variations the device includes a shaft having a proximal end and a distal end, where the shaft proximal end may be coupled to the distal end of the handle, and the shaft distal end may be coupled to a cleansing tip. For example, as shown in FIG. 12 A, debridement device (2000) includes a handle (2002) having a distal end (2004). The proximal end (2008) of a shaft (2006) is coupled to the handle distal end (2004). The distal end (2010) of the shaft (2006) is coupled to a cleansing tip (2012).

The shaft may be made from various materials. Similar to the handle, the shaft may be made from a plastic material such as styrene, acrylonitrile butadiene styrene (ABS), nylon, a polyolefin, or combinations thereof. The shaft may also be formed from a metal, a rubber material, compressed paper material, rolled paper material, wood, bamboo, other natural or synthetic materials, or combinations thereof.

The shaft may be provided in various lengths depending on such factors as the age of the user, the type of cleansing tip being employed, the handle design, and the body cavity being debrided. Additionally, in some embodiments, the shaft itself may serve as the handle with the tip(s) being directly connected or adherent to the shaft. The length of the shaft may range from about 1 cm to about 20 cm, including all values and sub-ranges in between. For example, handle length may be about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm.

In some instances, the shaft may be rigid. In other instances, the shaft may be malleable. Here the malleable shaft may be bent between about 10 degrees and about 30 degrees with respect to the axis of the handle to help facilitate entry into the body cavity or contact with the body cavity surface. For example, the shaft may be bent about 10 degrees, about 15 degrees, about 20 degrees, about 25 degrees, or about 30 degrees with respect to the axis of the handle.

The handle may be fixed to the proximal end of the shaft or removably coupled to the proximal end of the shaft. The handle may be removably coupled to the shaft via friction fit between the components, a threaded connection, or via one or more connector pieces, for example, male-female connectors or other complementary shaped fittings.

A locking mechanism may also be provided on the handle to secure it to the shaft. The locking mechanism may be helpful when the device is used to cleanse the vaginal cavity. For example, referring to FIG. 11B, shaft (1000) includes a proximal end (1002) shaped to interlock with handle (1004) when inserted into slot (1006) having a complementary shape. Depression of tab (1008) on the handle (1004) depresses the shaped proximal end (1002) to thereby release it from the handle (1004). In another variation, as shown in FIG. 11A, handle (1010) comprises a button (1012) including a stem (1014) that interlocks with hole (1016) in the shaft (1018) when the proximal end (1022) of the shaft (1018) is inserted into slot (1020) of handle (1010). Other attachment methods such as press-fit and friction fit may be employed as well. In these instances the shaft may be secured by pressing the shaft firmly into the handle, and may be released by firmly pulling the shaft from the handle.

Cleansing Tips

Figure 2B:
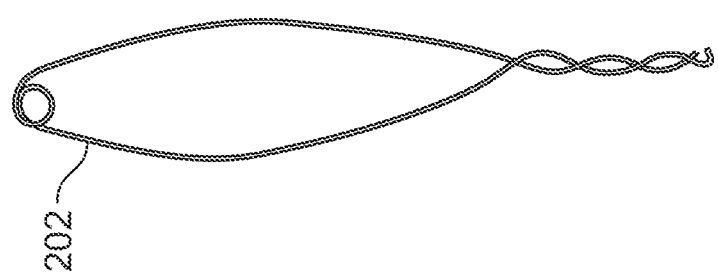
Figure 2A:
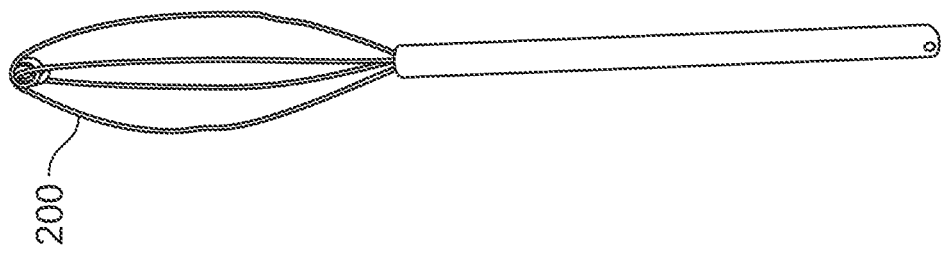
Figure 1:
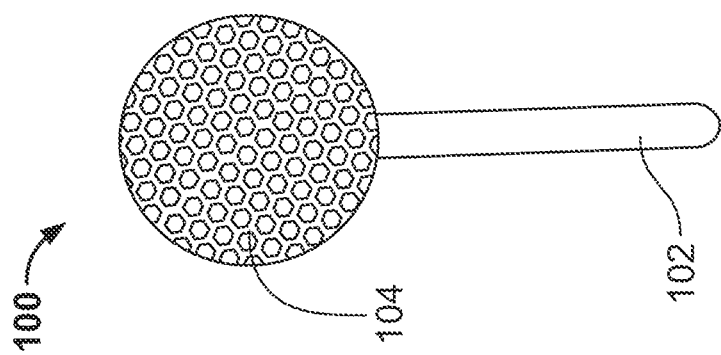
FIG. 1 depicts an exemplary cleansing device including a handle and a cleansing tip having a circular shape.

The devices described herein may include one or more cleansing tips. The one or more cleansing tips may be directly coupled to the distal end of the handle. For example, as shown in FIG. 1, a simple debridement device (100) may include a handle (102) and a cleansing tip (104). However, as previously stated, and as shown in FIG. 12A, some variations of the device include a shaft having a proximal end and a distal end, where the shaft proximal end may be coupled to the distal end of the handle, and the shaft distal end may be coupled to a cleansing tip. The cleansing tip may be fixed to the distal end of the shaft or slidable over the distal end of the shaft. In some variations, the shaft distal end may include a shaped scaffold so that when the cleansing tip is slid over the distal end of the shaft, it takes the shape of the scaffold. For example, as shown in FIG. 2A, the cleansing tip may include an elliptically shaped scaffold (200). In another variation, as shown in FIG. 2B, the cleansing tip may include an oval shaped scaffold (202). A cleansing tip material may be provided on the oval shaped scaffold (202), e.g., formed on the scaffold or slid onto the scaffold, so that the material takes the shape of the oval shaped scaffold (202), as illustrated in FIG. 2C.

The cleansing tips may have various shapes and may be made from various materials. For example, the cleansing tips may have cleansing surfaces that are conical, round (circular), ovular, rectangular, or triangular in shape. The cleansing tip may be made from various materials such as polymer materials or natural materials. Exemplary polymer materials include without limitation, foam, polyamides, polyesters, rubber, nylon, polypropylene, thermoplastic elastomers, silicones, polyurethanes, or combinations thereof. Exemplary natural materials include without limitation, bamboo, cotton, linen, wool, or a combination thereof. In some variations, the cleansing tip is formed from material or filaments that have been twisted, helically wound, felted, braided or injection molded with thermoplastic elastomer material. With respect to thermoplastic elastomers, the desired flexibility of the tips may be modified by changing the thickness and/or the durometer of the materials. In one variation, the thermoplastic elastomer may have a durometer ranging between about 10 Shore A to about 30 Shore A to achieve the desired flexibility while maintaining adequate stiffness for debridement. For example, the durometer may be about 10 Shore A, about 11 Shore A, about 12 Shore A, about 13 Shore A, about 14 Shore A, about 15 Shore A, about 16 Shore A, about 17 Shore A, about 18 Shore A, about 19 Shore A, about 20 Shore A, about 21 Shore A, about 22 Shore A, about 23 Shore A, about 24 Shore A, about 25 Shore A, about 26 Shore A, about 27 Shore A, about 28 Shore A, about 29 Shore A, or about 30 Shore A. When the cleansing tips include a plurality of leaflets disposed in a direction parallel to the axis of the handle, the tips may have a durometer of about 14 A. When the cleansing tips include a plurality of leaflets disposed helically about the axis of the handle, the tips may have a durometer of about 22 A. Similar to the handle, the cleansing tip may be reusable or disposable.

Figure 3B:
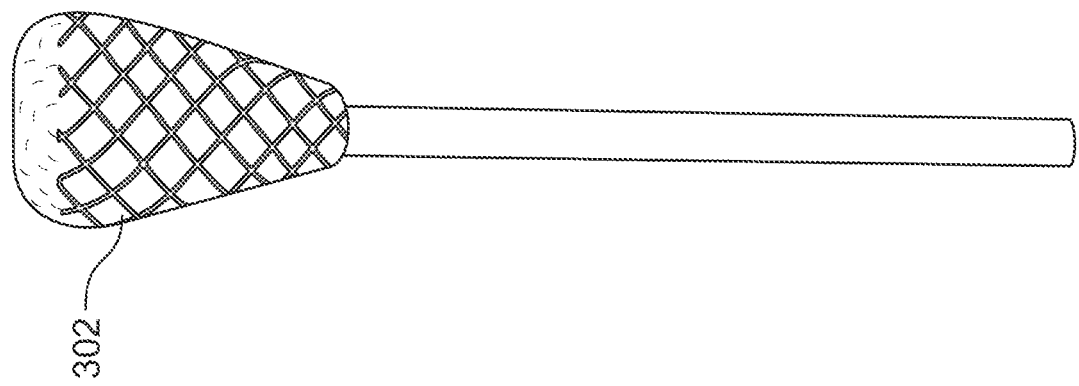
FIG. 3B depicts an exemplary cleansing tip having a conical shape.
Figure 3A:
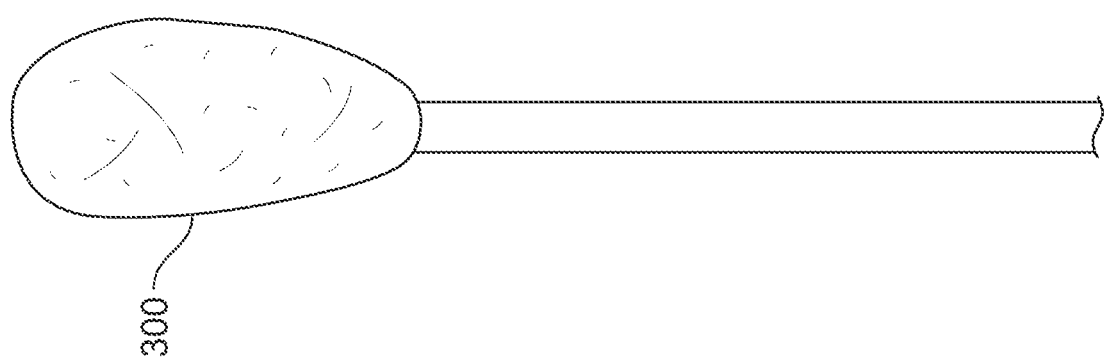
FIG. 3A depicts an exemplary cleansing tip having a bulbous shape.
Figure 4B:
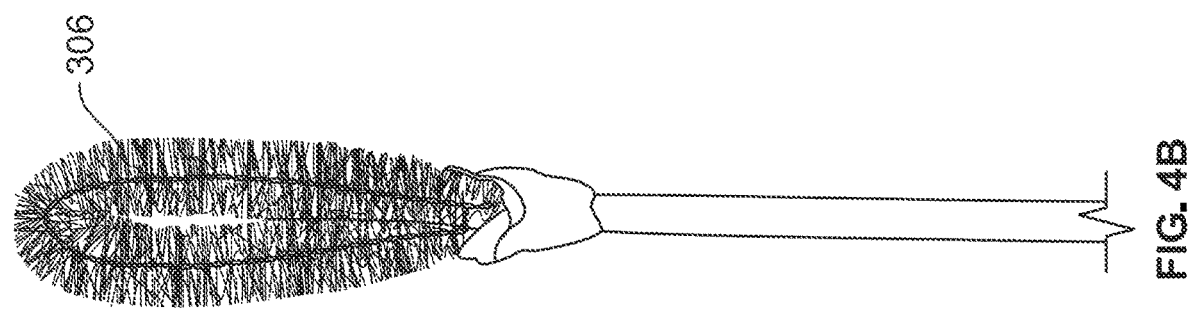
FIGS. 4A and 4B depict exemplary cleansing tips comprising a loop of material.
Figure 4A:
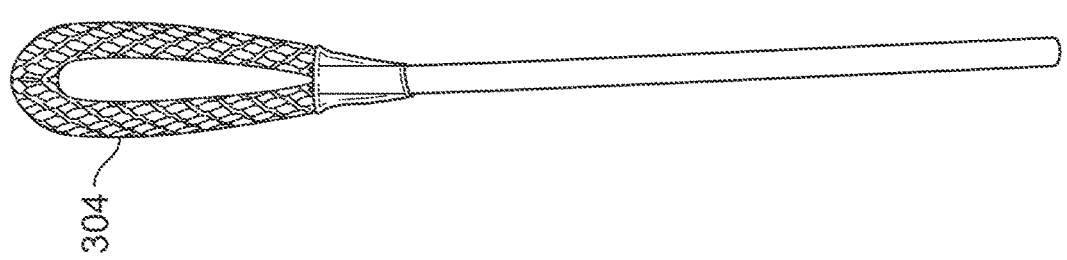
Figure 7C:
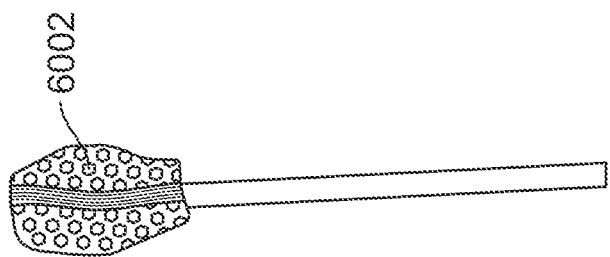
FIGS. 7A-7C depict further exemplary shapes and configurations for the cleansing tip.
Figure 7B:
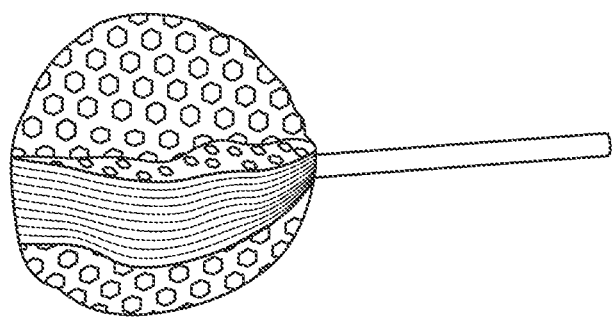
Figure 7A:
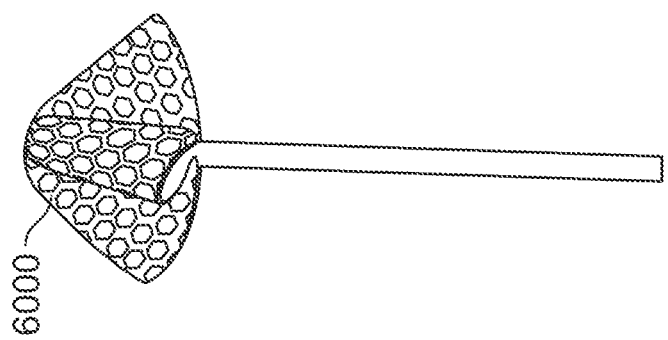
Figure 8C:
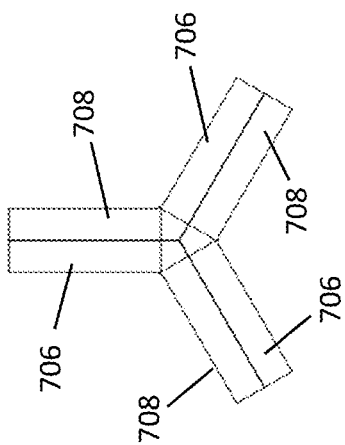
FIGS. 8A-8N depict yet further exemplary cleansing tips including a plurality of leaflets.
Figure 8B:
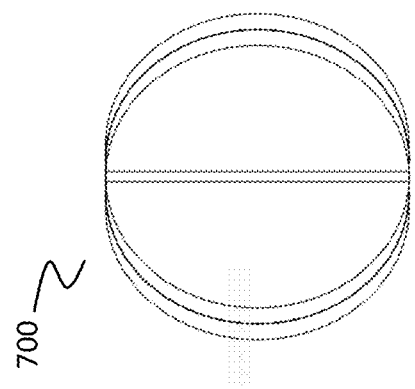
Figure 8A:
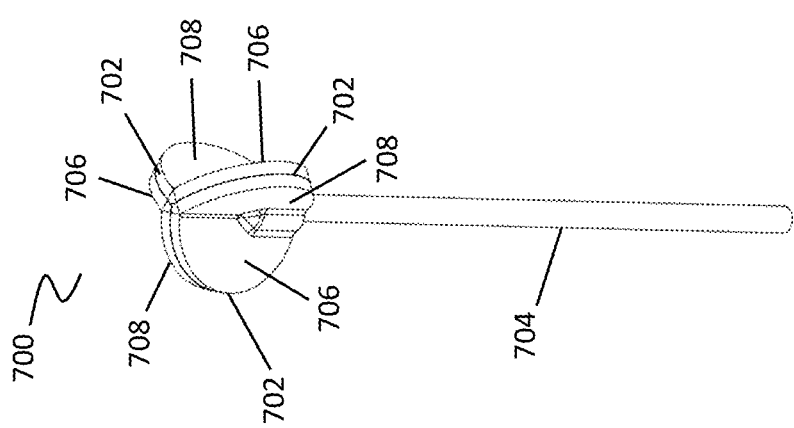
Figure 8H:
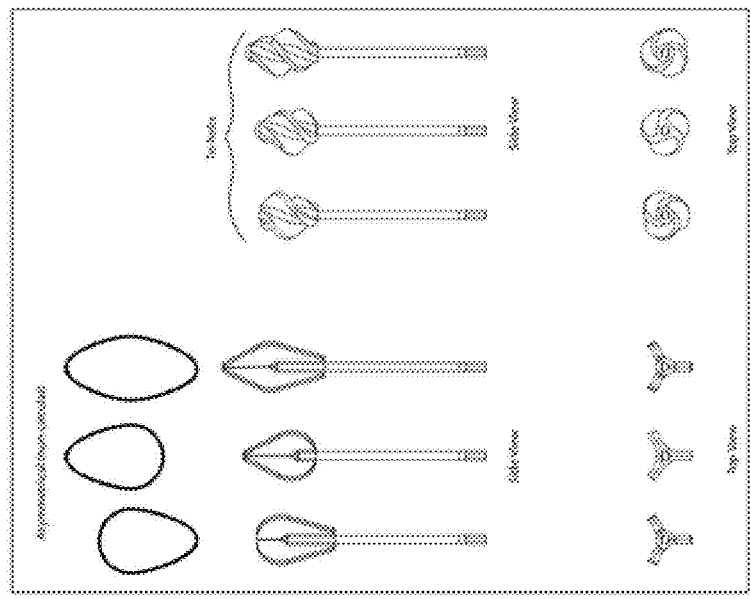
Figure 8G:
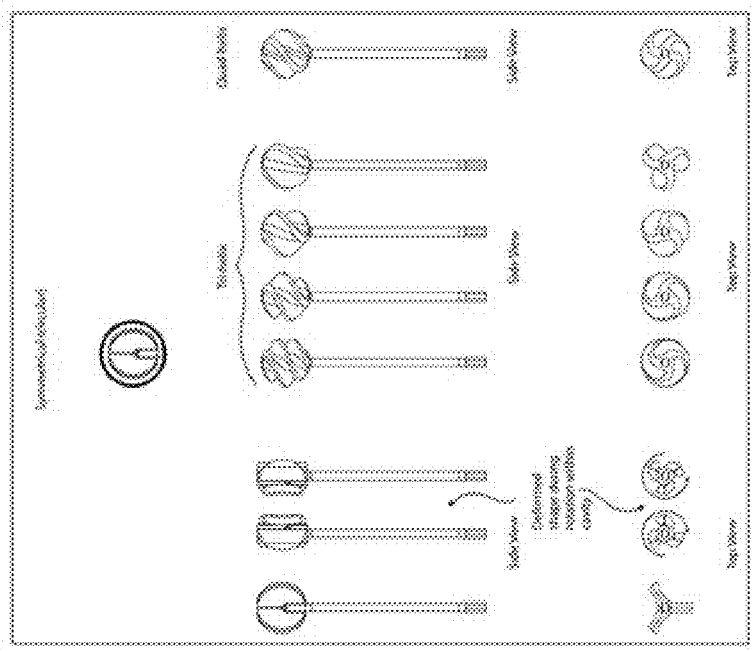
Figure 18:
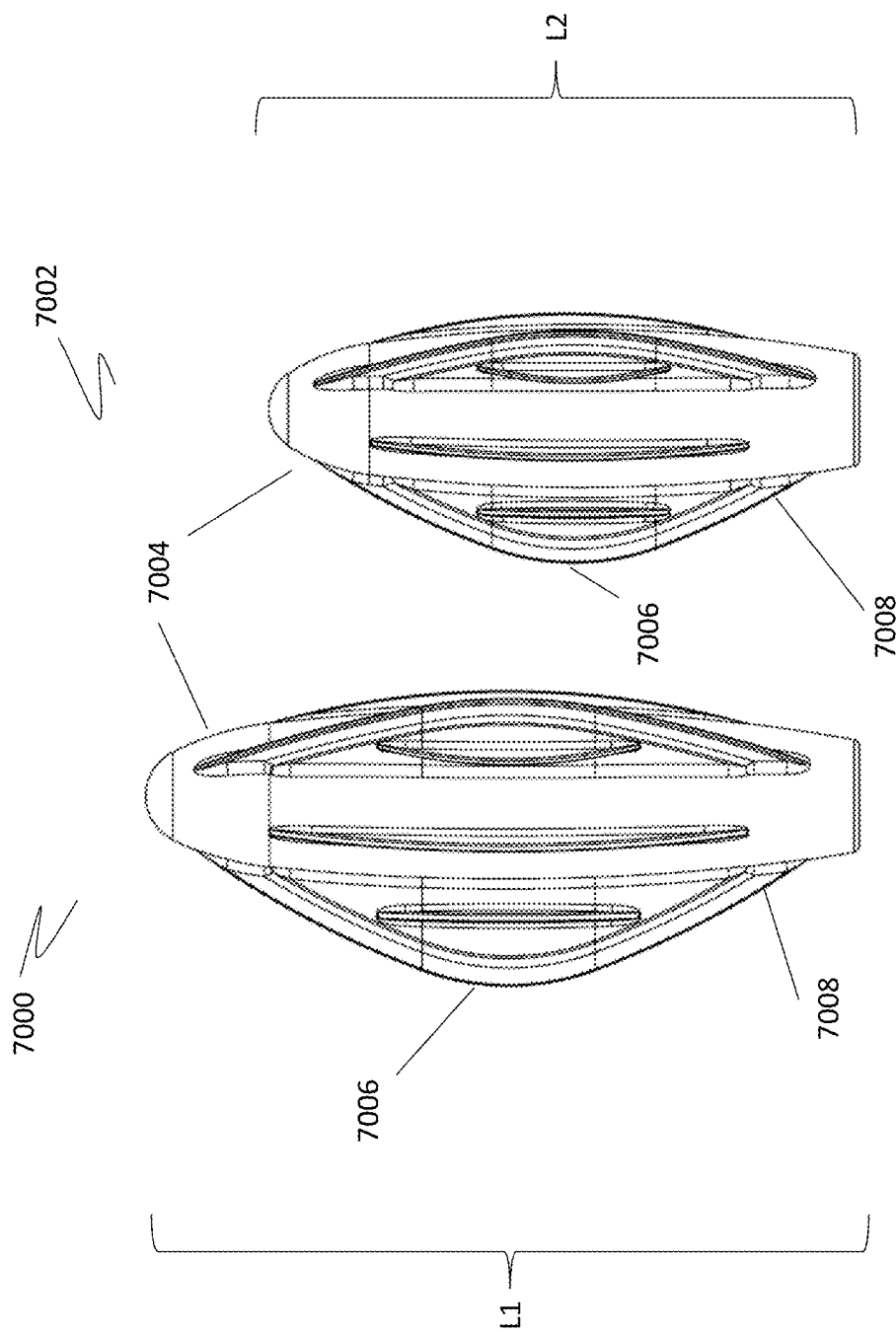
FIG. 18 depicts an exemplary adult and pediatric cleansing tip having a an expanded center portion that may serve as a safety feature.

In other variations, the profile of the cleansing tip is symmetrical or circular (see, e.g., FIGS. 7B and 8G). In further variations, the profile of the cleansing tip is asymmetrical or non-circular (see, e.g., FIG. 8H). Here one end of the cleansing tip may be tapered, or both of the cleansing tip ends may be tapered (see, e.g., element 6002 in FIG. 7C). Other cleansing tip shapes and configurations include a bulbous shape (300) (FIG. 3A), a conical shape (302) (FIG. 3B), or a loop shape (FIGS. 4A and 4B). In FIG. 4A, the cleansing tip comprises a loop (304) made from braided filaments. In FIG. 4B, the cleansing tip comprises a loop (306) made from a bristled material. The cleansing tip may also have an umbrella shape (6000) (FIG. 7A). These shapes may conform to the particular anatomic location meant to be cleansed with the device, and the shape may assist in preventing injury of the particular body cavity by limiting the depth of penetration into the body cavity. For example, as shown in FIG. 18, cleansing tips (7000, 7002) may include a narrow distal tip (7004), an expanded center portion (7006), and a narrow proximal end (7008). When inserted into the nasal cavity, for example, the expanded center portion (7006) may help prevent the distal tip (7004) from being inserted too far into the nasal passage, and may thereby function as a safety feature.

The length of the cleansing tips may also vary depending on such factors as the age of the patient or user, and/or the body cavity surface to be cleansed. For example, the length of the cleansing tip may be longer for an adult user, and shorter for a pediatric user. The cleansing tip length may range from about 25 mm to about 30 mm for an adult user, including all values and sub-ranges in between. For example, the adult cleansing tip may have a length of about 25 mm, about 26 mm, about 27 mm, about 28 mm, about 29 mm, or about 30 mm. The cleansing tip length may range from about 10 mm to about 25 mm for a pediatric user, including all values and sub-ranges in between. For example, the pediatric cleansing tip may be about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm. Referring to FIG. 18, the length (L1) of adult cleansing tip (7000) is about 29 mm, and the length (L2) of pediatric cleansing tip (7002) is about 24 mm. The percent reduction of the pediatric tip (7002) to the adult tip (7000) may be about 18 percent.

Figure 19B:
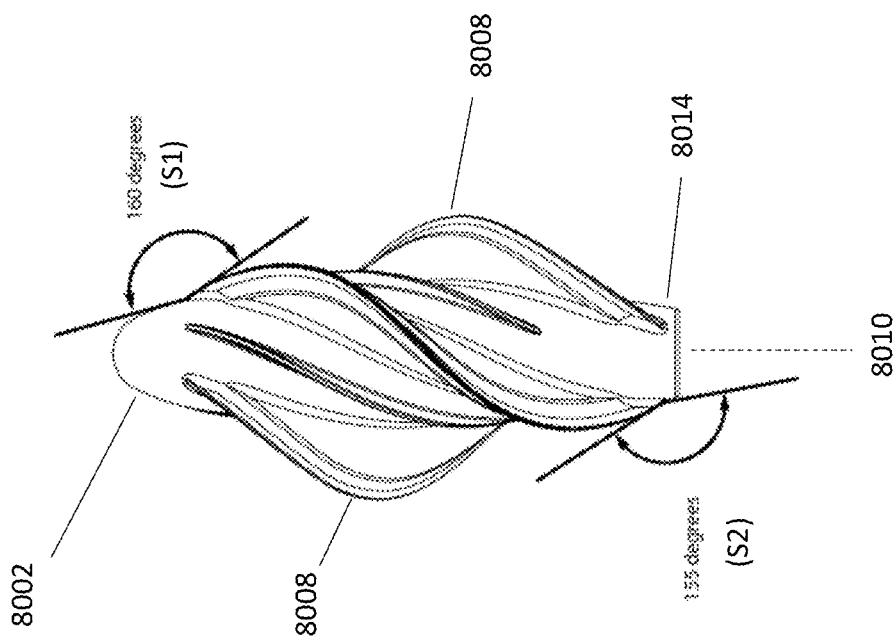
FIGS. 19A and 19B depict exemplary angles at which the leaflets emerge from the distal tip and proximal end of cleansing tips.
Figure 19A:
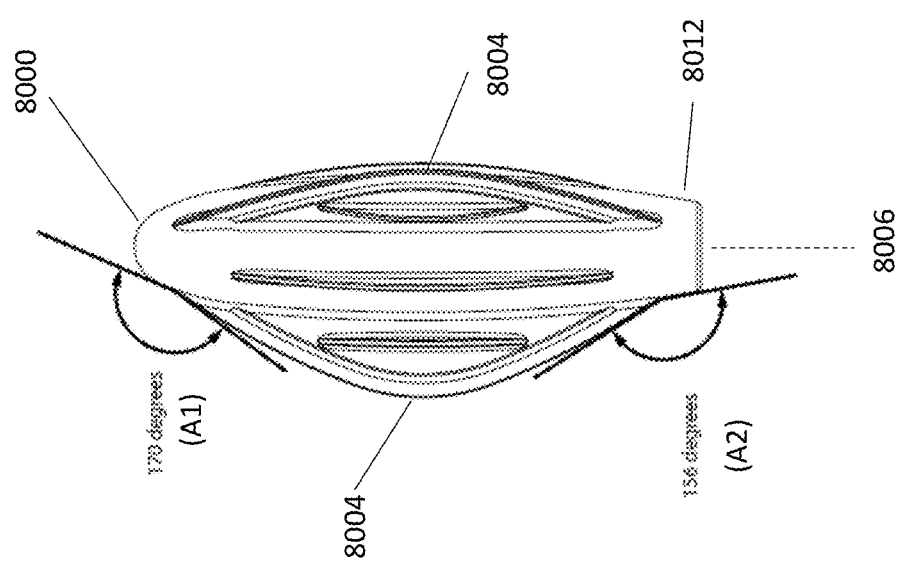

Furthermore, the configuration of the flexible leaflets as they emerge from the distal tip and/or the proximal end of a cleansing tip may allow the tip to reach the most inaccessible regions of the nostril for cleansing, debridement, and/or or delivery of substances such as antiseptics, antibiotics, etc. One example is the cul-de-sac of the inner aspect of the tip of the nose where bacteria and viruses can accumulate. Another example is the interstices of the vaginal walls that create folds where bacteria, fungi, and yeast may accumulate and be difficult to eliminate with lavage or simply inserting antimicrobial substances. The angle at which the leaflets emerge (emergence angle) from the distal tip may range from about 150 degrees to about 170 degrees, including all values and sub-ranges in between. This angle is measured between the two tangent lines extending from the point at which the leaflet and distal tip surface meet, excluding the fillet (rounding) between surfaces. For example, the angle may be about 150 degrees, about 151 degrees, about 152 degrees, about 153 degrees, about 154 degrees, about 155 degrees, about 156 degrees, about 157 degrees, about 158 degrees, about 159 degrees, about 160 degrees, about 161 degrees, about 162 degrees, about 162 degrees, about 163 degrees, about 164 degrees, about 165 degrees, about 166 degrees, about 167 degrees, about 168 degrees, about 169 degrees, or about 170 degrees. When the leaflets are disposed parallel to the axis of the handle, they may emerge or begin about 2.0 mm from the distal tip, and emerge or begin about 2.0 mm from the proximal end. When the leaflets are disposed in a helical manner about the axis of the handle, they may emerge or begin about 3.5 mm from the distal tip, and emerge or begin about 0.8 mm from the proximal end. As shown in FIG. 19A, the angle (A1) of leaflet emergence from the distal tip (8000) may be about 170 degrees for a cleansing tip having leaflets (8004) that are disposed parallel to the axis (8006) of the handle (not shown). As shown in FIG. 19B, the angle (S1) of leaflet emergence from the distal tip (8002) may be about 160 degrees for a cleansing tip having leaflets (8008) that are disposed in a helical manner about the axis (8010) of the handle (not shown). The angle at which the leaflets emerge from the proximal end of the cleansing tip may range from about 150 degrees to about 160 degrees, including all values and sub-ranges in between. For example, the angle may be about 150 degrees, about 151 degrees, about 152 degrees, about 153 degrees, about 154 degrees, about 155 degrees, about 156 degrees, about 157 degrees, about 158 degrees, about 159 degrees, or about 160 degrees. This angle is measured between the two tangent lines extending from the point at which the leaflet and proximal end surface meet, excluding the fillet (rounding) between surfaces. As shown in FIG. 19A, the angle (A2) of leaflet emergence from the proximal end (8012) may be about 156 degrees for a cleansing tip having leaflets (8004) that are disposed parallel to the axis (8006) of the handle (not shown). As shown in FIG. 19B, the angle (S2) of leaflet emergence from the proximal end (8014) may be about 155 degrees for a cleansing tip having leaflets (8008) that are disposed in a helical manner about the axis (8010) of the handle (not shown).

Figure 20:
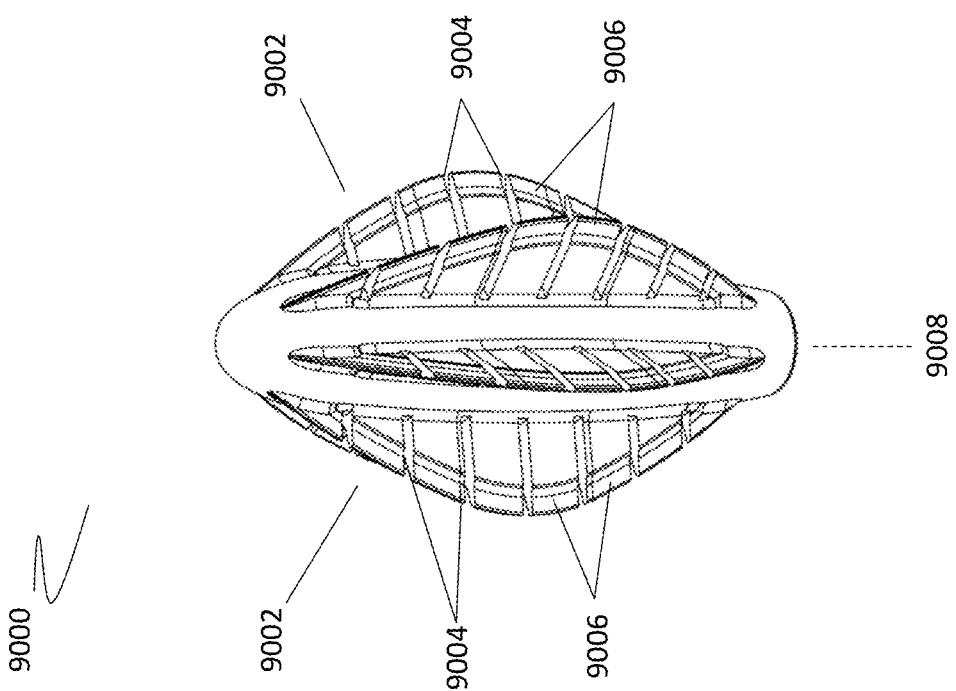
FIG. 20 depicts an exemplary cleansing tip including leaflets having separations that divide the leaflets into portions.

In some variations, the leaflets of a cleansing tip may include one or more features that increase the amount of body cavity surface debridement. For example, as shown in FIG. 20, cleansing tip (9000) may include a plurality of leaflets (9002) having one or more separations ("cuts") (9004) that divide the leaflets (9002) into portions (9006). Any number of separations may be employed to create the desired number of leaflet portions. Each leaflet may have separations that are the same length or different lengths. The separations or cuts may also be made at various angles with respect to the axis of the handle. For example, the separation or cut may form a 45 degree, a 60 degree, or a 90 degree angle with the axis (9008) of the cleansing device handle. Referring to FIG. 20, separations (9004) form a 90 degree angle with respect to the axis (9008) of the handle (not shown).

Figure 21:
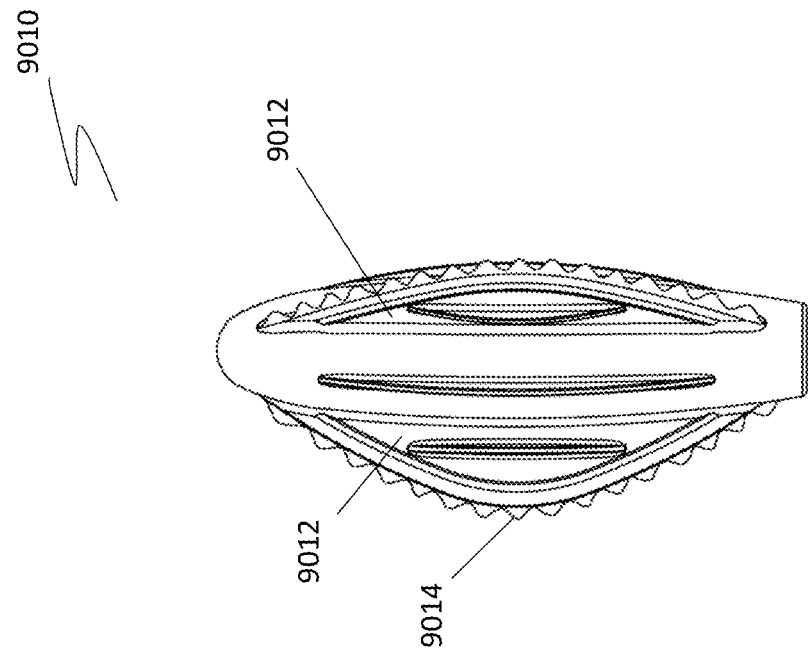
FIG. 21 depicts an exemplary cleansing tip including leaflets having a serrated edge.

Alternatively, devices that increase the amount of debridement may include one or more leaflets having an irregular edge or a sharp, cutting edge. The cutting edge may span the entire length of the leaflet or a portion thereof. In one variation, the cutting edge may comprise a serrated edge. The teeth of the serration may all have the same durometer, or some teeth may have a different durometer than other teeth. In some variations, the teeth may be glued onto the leaflet. In other variations, the teeth may be injection molded onto the leaflet. In further variations, the teeth may be 3D printed onto the leaflet. For example, as illustrated in FIG. 21, cleansing tip (9010) may include a plurality of leaflets (9012) having a serrated edge (e.g., teeth at the leading edge of the leaflet) (9014). Although shown as uniform in height, the teeth of the serrated edge may have varying heights.

Figure 23:
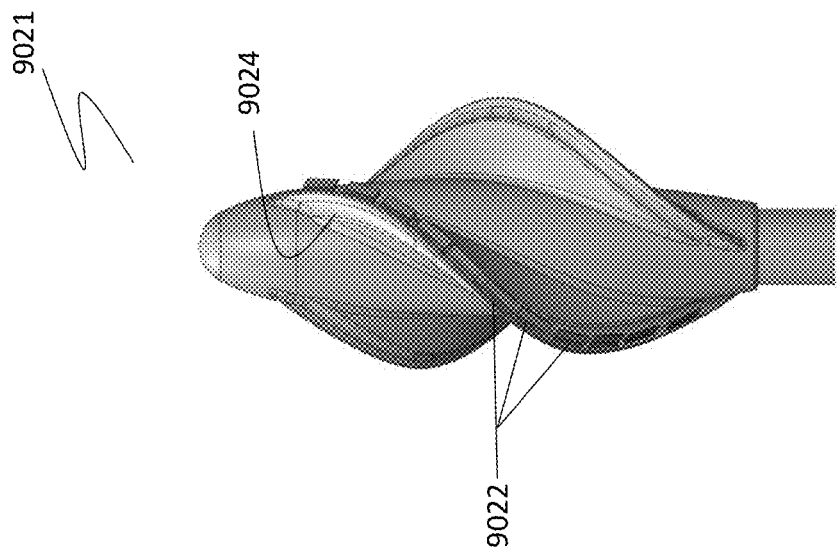
FIG. 23 depicts an exemplary cleansing tip including a plurality of individual blades disposed along the leaflet edge.
Figure 22:
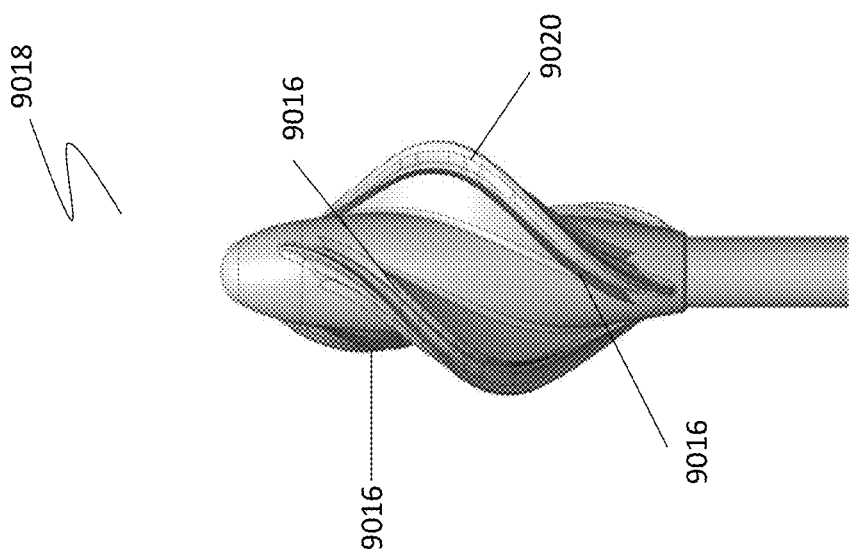
FIG. 22 depicts an exemplary cleansing tip including helical blades disposed about tip.

In yet further variations, as illustrated in FIGS. 22 and 23, the cutting edge may be formed by one or more blades on the leaflet. The blades may be made from various materials such as stainless steel and alloys thereof, a ceramic, or a polymeric material. The blades may also be positioned at the leaflet edge or spaced a distance from the edge. The one or more blades may be coupled to the leaflets by gluing or embedding the blade within the material of the leaflet. Additionally, the blades may be variously sized and shaped depending on the body surface it is intended to debride or on the type of debris it is intended to remove. For example, the one or more blades may be rectangular, square, triangular, spiral or helical shaped, or arc shaped. The one or more blades may also be spaced along the leaflet edge, or spaced from the leaflet edge in various ways. For example, the one or more blades may be spaced between about 0.5 mm to about 2.0 mm from the leaflet edge, including all values and sub-ranges in between. For example, the one or more blades may be spaced from the leaflet edge about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm. When a plurality of blades are employed, the blades may be uniformly spaced or irregularly spaced along the leaflet edge. Referring to FIG. 22, a plurality of helical blades (9016) are disposed about cleansing tip (9018). The helical blades (9016) are positioned at the leaflet edge (9020) for each leaflet of the cleansing tip (9018), and run continuously along the edge (9020). In some variations, as shown in FIG. 23, cleansing tip (9021) may include a plurality of individual blades (9022) at the leaflet edge (9024). The individual blades (9022) are uniformly spaced along edge (9024) and run along the entire length of edge (9024). When a blade is provided on the leaflet, the cleansing tip may also function as a shaver to remove hair within the nasal cavity.

Figure 5D:
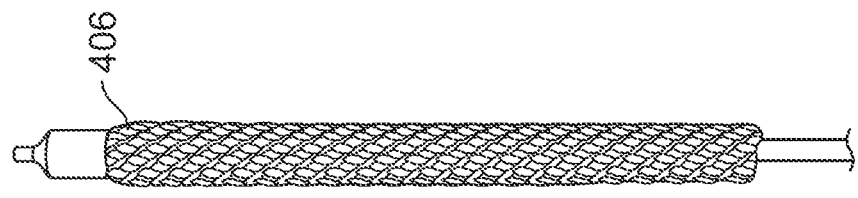
FIGS. 5A-5D depict exemplary cleansing tips comprising twisted, helically wound, or braided material.
Figure 5C:
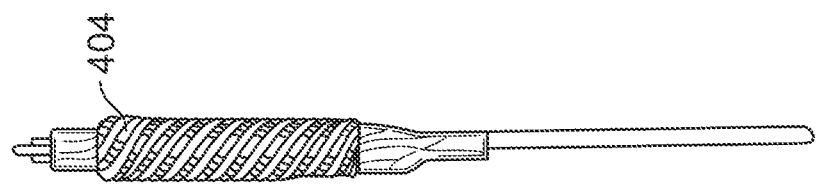
Figure 5B:
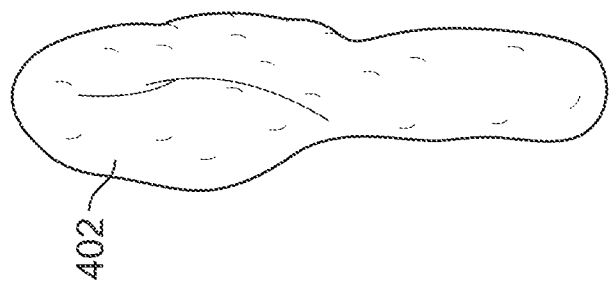
Figure 5A:
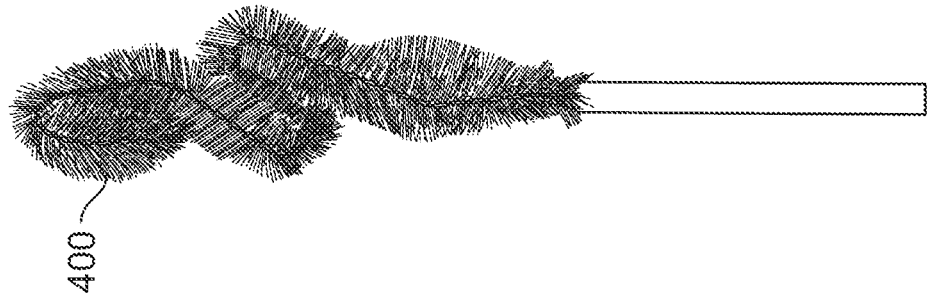

In yet further variations, the cleansing tip may be formed from a twisted bristled material (400) (FIG. 5A), a twisted tufted material (402) (FIG. 5B), a plurality of helically wound filaments (404) (FIG. 5C), or braided filaments (406) (FIG. 5D).

Figure 6C:
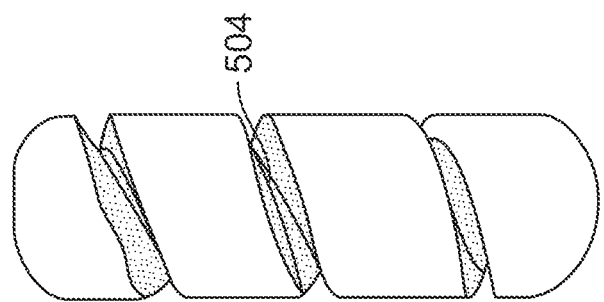
FIGS. 6A-6C depict exemplary cleansing tips including one or more grooves or channels.
Figure 6B:
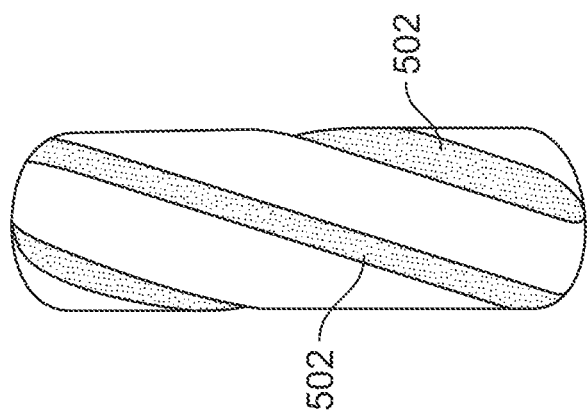
Figure 6A:
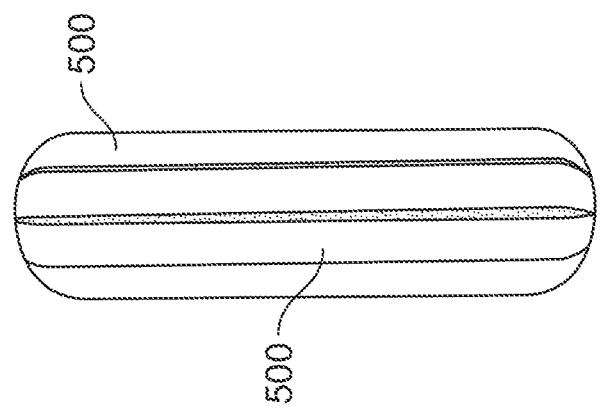

Some variations of the cleansing tip are made from a foam. The foam tip may include one or more channels or grooves to texturize the tip surface. Referring to FIGS. 6A to 6C, the foam tip may include a plurality of longitudinal grooves or channels (500) (FIG. 6A), a plurality of diagonally or spirally running grooves or channels (502) (FIG. 6B), or a single groove or channel (504) extending helically around the tip (FIG. 6C). The foam itself may be of an "open cell architecture" thereby inherently having a rough surface that accomplishes the debridement, or a closed cell foam with a skinned surface, with or without a dimpled or textured skin surface.

When the cleansing tip is made from a polymer, the leaflets may be helically disposed about the tip (and axis of the handle), or disposed parallel to the axis of the handle. Leaflets having other orientations with respect to the distal tip and/or handle axis may also be made from a polymer. Such tips may be cast from molds, injection molded, or 3D printed. The height of the polymeric tip may range from about 10 mm to about 35 mm, including all values and sub-ranges in between. For example, the polymeric tip height may be about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, or about 35 mm. The width of the polymeric tip may range from about 10 mm to about 25 mm, including all values and sub-ranges in between. For example, the width of the polymeric tip may be about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm. Regarding leaflet thickness for the polymeric tips, it may range from about 0.2 mm to about 3.0 mm, including all values and sub-ranges in between. For example, leaflet thickness may be about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, or about 3.0 mm. In one variation, the polymeric tip may have a height of about 28 mm, a width of about 18 mm, and a leaflet thickness of about 3.0 mm. In another variation, the polymeric tip may have a height of about 33 mm, a width of about 18 mm, and a leaflet thickness of about 3.0 mm. In a further variation, the polymeric tip may have a height of about 30 mm, a width of about 16 mm, and a leaflet thickness of about 3.0 mm. In yet a further variation, the polymeric tip may have a height of about 30 mm, a width of about 16 mm, and a leaflet thickness of about 2.5 mm. In some variations, the polymeric tip may have a height of about 28 mm, a width of about 15 mm, and a leaflet thickness of about 2.5 mm. In other variations, the polymeric tip may have a height of about 29 mm, a width of about 15.5 mm, and a leaflet thickness of about 0.2 mm. Pediatric variations of the polymeric tip may have a height of about 24 mm, a width of about 12.5 mm, and a leaflet thickness of about 0.2 mm. The distal end of the polymeric tips may also include varying radiuses of curvature, and may be more rounded or have more or less of a point depending on the cavity or anatomical area being cleansed.

The distal end of the leaflets may also emerge from the tip at various locations or positions along the length of the tip. For example, some may emerge more distally or more proximally than others along the length of the tip. Likewise, the proximal end of the leaflets may end at various locations or positions along the tip length. As previously described, when the leaflets are disposed parallel to the axis of the handle, they may emerge or start at various points along the length of tip, including from the very point of the tip to about 2.0 mm proximal from the distal tip, and end about 2.0 mm from the proximal end. When the leaflets are disposed in a helical manner about the axis of the handle, they may emerge or start at various points along the length of tip, including from the very point of the tip to about 3.5 mm proximal from the distal tip, and end about 0.8 mm from the proximal end.

Figure 16A:
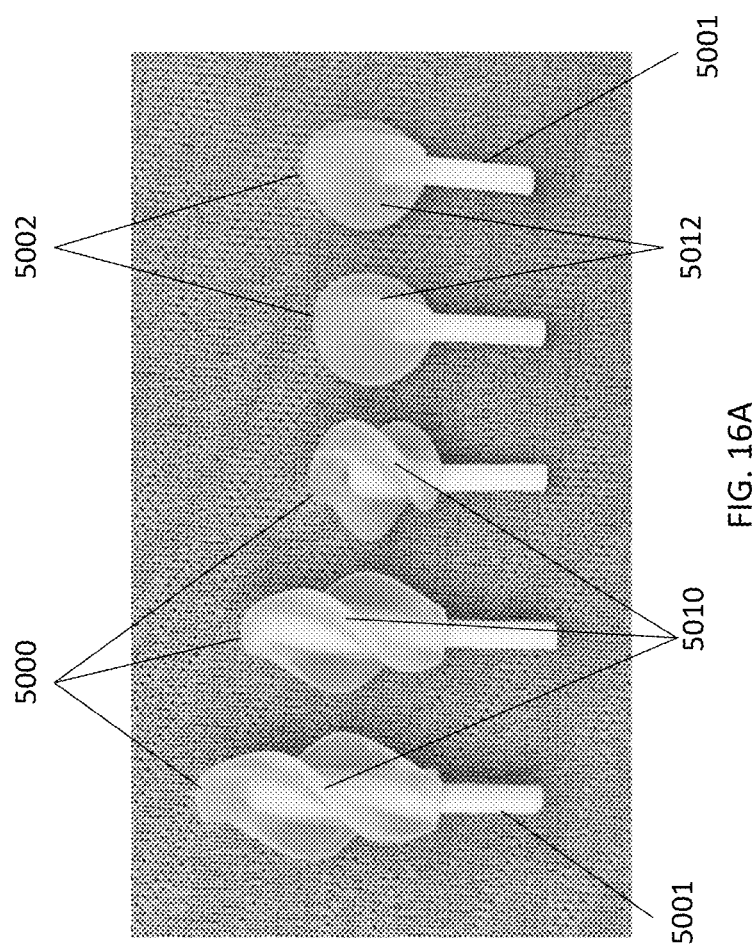
Figure 16C:
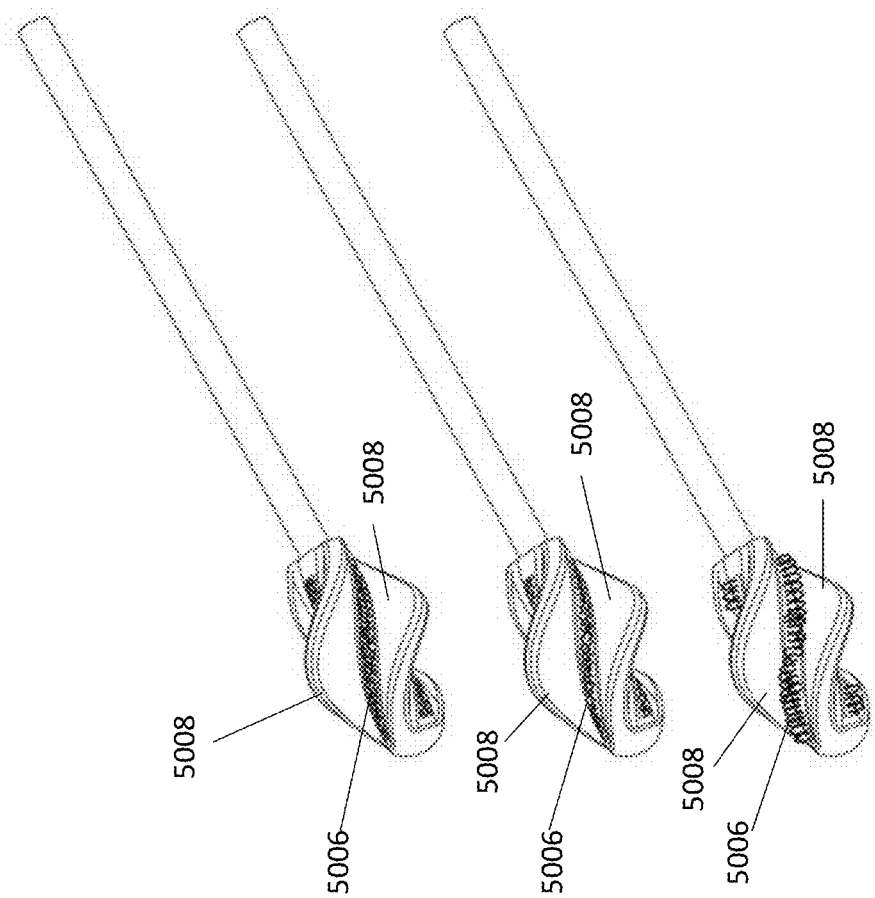
Figure 17:
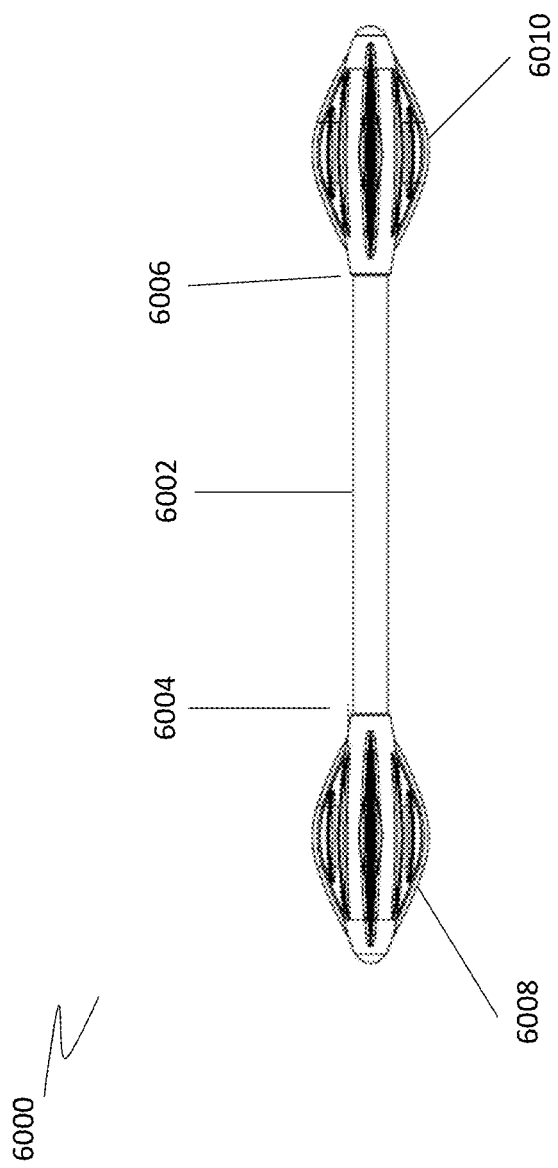
FIG. 17 depicts an exemplary device including a handle and two cleansing tips.

FIG. 16A shows exemplary cleansing tips that may be made from a polymer. These polymeric cleansing tips may have leaflets (5010) configured in a helical pattern about the tip (e.g., tips 5000), and may be provided in varying sizes. The polymeric tips may also have rounded leaflets (5012) that run parallel to the shaft (e.g., tips 5002). Additionally, the polymeric tips may have a texture (5004), as shown in FIG. 16B. When configured in a helical pattern, the polymeric tips may include openings or windows (5006) between the leaflets (5008). These openings or windows may also allow texturing or a material to show through. The material may be different from the material of the polymeric tip, and may be fibrous, for example, made from cotton or other fleecing. In one variation, the polymeric tip including openings is slid over a shaft including texturing or a fibrous material at its distal end such that the texturing or material shows through the openings. The polymeric tips may be provided with any suitable number of openings or windows.

In general, the length of the cleansing tip may vary depending on such factors as the age of the user, the type of cleansing surface employed, and the size of the body cavity being debrided. In general, the length of the cleansing tip may range from about 0.5 cm to about 8.0 cm, including all values and sub-ranges in between. For example, the length of the cleansing tip may be about 0.5 cm, about 0.6 mm, about 0.7 mm, about 0.8 mm, about 0.9 mm, about 1.0 cm, about 1.5 cm, about 2.0 cm, about 2.5 cm, about 3.0 cm, about 3.5 cm, about 4.0 cm, about 4.5 cm, about 5.0 cm, about 5.5 cm, about 6.0 cm, about 6.5 cm, about 7.0 cm, about 7.5 cm, or about 8.0 cm. When the cleansing tip has a circular profile, the diameter of the tip may range from about 1.0 cm to about 4.0 cm, including all values and sub-ranges in between. For example, the diameter of the tip may be about 1.0 cm, about 1.5 cm, about 2.0 cm, about 2.5 cm, about 3.0 cm, about 3.5 cm, or about 4.0 cm.

The plurality of cleansing surfaces of the cleansing tip are generally sufficiently rigid to allow debridement, but flexible enough so that different sets of cleansing surfaces may be exposed upon movement of the tip in opposing directions. For example, clockwise and counterclockwise rotation, or translation back and forth along a linear axis may allow transition between a first set of cleansing surfaces and a second set of cleansing surfaces. The type of material employed to make the cleansing surfaces and/or thickness of material used to make the cleansing surfaces may be adjusted to achieve the desired amount of flexibility and rigidity. More specifically, the amount of flexibility may be adjusted by varying a combination of factors, e.g., by varying the geometry, size, and/or shape of the cleansing surfaces, and by varying the thickness and/or stiffness of the material used to make the cleansing surfaces. The material(s) could have a variable stiffness due to overmolding, overlaying, dipping, or coextrusion of two or more materials of differing stiffness. Also, the thickness of the plurality of cleansing surfaces could be uniform, non-uniform, or highly variable to modify the apparent rigidity of the geometry. Flexibility of the cleansing surfaces may also be adjusted so that they conform to the shape of the body cavity. The shape of the cleansing surfaces may also contribute to how well they conform to the surface of the body cavity and debride the surface of the body cavity.

The plurality of cleansing surfaces may be variously disposed about the axis of the handle. For example, the plurality of cleansing surfaces may be disposed in a direction parallel to the axis of the handle. This orientation may be beneficial when the device is used to cleanse the nasal cavity. Alternatively, the plurality of cleansing surfaces may be disposed in a direction perpendicular to the axis of the handle. The perpendicular orientation may be beneficial when the device is used to cleanse the vaginal cavity. In some variations, the cleansing surfaces are disposed helically about the axis of the handle. Additionally, the cleansing surfaces may be variously spaced about the cleansing tip. For example, the plurality of cleansing surfaces may be equally spaced apart about the cleansing tip or unequally spaced apart about the cleansing tip.

Some variations of the cleansing tip include a plurality of leaflets, where the cleansing surfaces are surfaces of the leaflets. For example, a first set of cleansing surfaces may be on a first side of the plurality of leaflets, and a second set of cleansing surfaces may be on a second side of the plurality of leaflets. In one variation, the texture of the leaflet surface is modified to aid in the debridement of the body cavity surfaces. For example, a plurality of bumps, nubs, protrusions, bristles, microneedles, barbs, small indentations, holes, and the like, may be disposed on one or more surfaces of the leaflets to roughen the surface(s). The texture may be provided over the entire surface of the leaflet or on portions thereof. In some variations, the texture is disposed in a pattern on the leaflet surface.

In general, both the durometer of the material as well as the thickness of the leaflets can help to determine the flexibility of the tips. The thickness of the leaflets may vary depending on amount of flexibility desired. For example, leaflet thickness may range from about 0.2 mm to about 5.0 mm, including all values and sub-ranges in between. For example, the thickness of the leaflets may be about 0.2 mm, about 0.3 mm, about 0.4 mm, about 0.5 mm, about 1.0 mm, about 1.5 mm, about 2.0 mm, about 2.5 mm, about 3.0 mm, about 3.5 mm, about 4.0 mm, about 4.5 mm, or about 5.0 mm. Leaflet width may range from about 3.0 mm to about 10 mm, including all values and sub-ranged in between. For example, the width of the leaflets may be about 3.0 mm, about 4.0 mm, about 5.0 mm, about 6.0 mm, about 7.0 mm, about 8.0 mm, about 9.0 mm, or about 10 mm.

The leaflets may have a proximal end and a distal end. The leaflets may be shaped so that the proximal end may be tapered, the distal end may be tapered, or both the proximal and distal ends are tapered. Furthermore, the plurality of leaflets may form a cleansing tip having a conical, round, oval, rectangular, or triangular shape. The plurality of leaflets may include any suitable number of leaflets. For example, the plurality of leaflets may include two, three, four, five, or six leaflets. In one variation, the cleansing tip includes three leaflets. For example, referring to FIGS. 8A to 8C, cleansing tip (700) comprises three leaflets (702) disposed in a direction parallel to the axis of the shaft (704) as well as parallel to the axis of the handle (not shown), and is coupled to shaft (704). The leaflets (702) have a first set of cleansing surfaces (706) and a second set of cleansing surfaces (708). Referring to the side view in FIG. 8B, the cleansing tip (700) has a symmetric, circular profile. In FIG. 8C, a top view of the cleansing tip is provided showing the first set of cleansing surfaces (706) and the second set of cleansing surfaces (708), and that they are distinct from one another. The symmetric, circular profile of cleansing tips having three leaflets and four leaflets, and how they deform when rotated in the nasal cavity is also provided in FIG. 8G. As shown in FIG. 8G, the leaflets may be formed into a helical shape (tri helix or quad helix) or the leaflets can be fabricated into a radial pattern, generally emanating from a central axis.

Cleansing tips having an asymmetric profile are shown in FIGS. 8D to 8F. Referring to those figures, the cleansing tips include three leaflets disposed in a direction parallel to the axis of the shaft (704) as well as parallel to the axis of the handle (not shown), and are coupled to shaft (704). In FIG. 8D, the leaflets (710) are tapered at one end (the proximal end 716), and comprise a first set of cleansing surfaces (712) and a second set of cleansing surfaces (714). In FIG. 8E, the leaflets (718) are tapered at the distal end (720), and comprise a first set of cleansing surfaces (722) and a second set of cleansing surfaces (724). In FIG. 8F, the leaflets (726) are tapered at both the proximal end (728) and distal end (730), and comprise a first set of cleansing surfaces (732) and a second set of cleansing surfaces (734). The asymmetric profile of cleansing tips having leaflets, and how they deform when rotated in the nasal cavity is also provided in FIG. 8H. These cleansing tips may be helpful when used, for example, to clean the skin, internal surface, and/or hair inside the nose to improve personal hygiene. As shown in FIG. 8H, the leaflets may be formed into an asymmetrical shape or a helical shape (tri-helix).

Figure 8K:
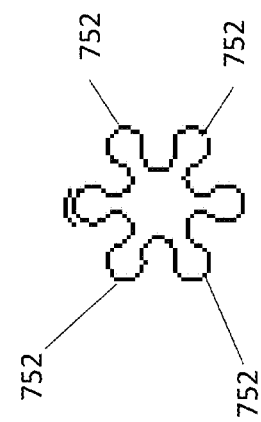
Figure 8N:
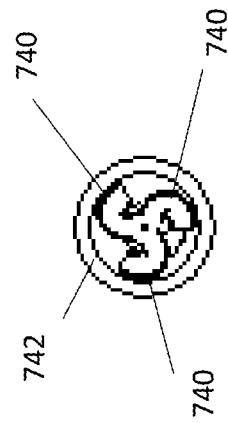
Figure 8J:
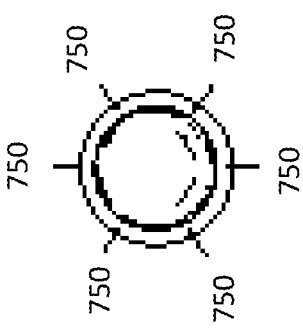
Figure 8M:
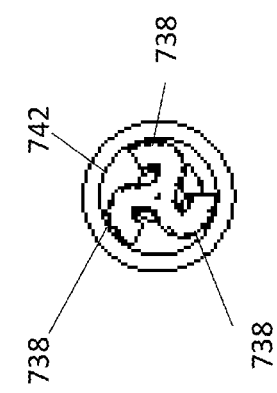
Figure 8I:
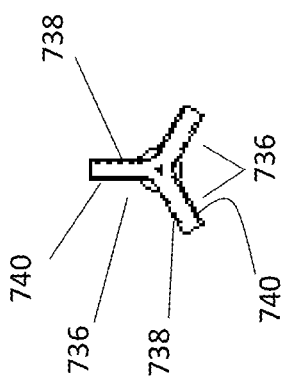
Figure 8L:
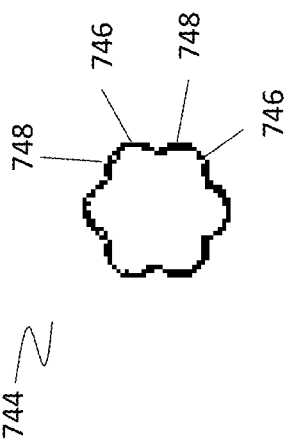

In some variations, the leaflets may comprise a plurality of bending elements having a first set of cleansing surfaces and a second set of cleansing surfaces. Any number of bending elements may be employed. For example, when the leaflets comprise bending elements, three or four bending elements may be employed. As shown in FIGS. 8I to 8K, each of the three leaflets may comprise a bending element (736). Each bending element (736) may include a first set of cleansing surfaces (738) and a second set of cleansing surfaces (740). Given the flexibility of the bending elements, when the cleansing tip is rotated clockwise within a cavity, as shown in FIG. 8J, the bending elements (736) bend or flex in a manner that allows the first set of cleansing surfaces (738) to contact the inner surface of a cavity (742) (or orifice). Rotation in the opposite, counterclockwise direction bends or flexes the bending elements (736) such that the second set of cleansing surfaces (740) contact the inner surface of the cavity (742) (or orifice), as shown in FIG. 8K. The bending elements may be provided in various shapes and sizes. For example, they may be linear (straight), curved, bulbous, etc. In one variation, the bending elements may be linear flexible members (e.g., as illustrated in FIGS. 8I to 8K). In another variation, the bending elements may be formed during rotation of the cleansing tip. In this variation, as shown in FIG. 8L, cleansing tip (744) includes first sections (746) that alternate with second sections (748). Areas of higher or increased flexibility are disposed between the first sections (746) and second sections (748) such that upon placement of the cleansing tip (744) within a smaller diameter cavity or orifice, as shown in FIG. 8M, the areas of increased flexibility (750) collapse to form bending members (752). The bending members (752) may then be rotated to cleanse the cavity or orifice. The alternating areas may include areas of different material, different texture, etc.

When the surface of the vaginal cavity is to be debrided, the devices may include a handle comprising a distal end, and a cleansing tip coupled to the distal end. The cleansing tip may include a plurality of leaflets, where the plurality of leaflets may comprise a first set of cleansing surfaces and a second set of cleansing surfaces. The first set of cleansing surfaces may remove debris from the vaginal cavity surface upon axial translation of the cleansing tip a first direction, and the second set of cleansing surfaces may remove debris from the vaginal cavity surface upon axial translation of the cleansing tip in a second opposite direction. Here the plurality of leaflets may be disposed in a direction perpendicular to the axis of the handle. In this variation, it may be beneficial for a locking mechanism to be provided for securing the handle to the shaft.

Figure 10A:
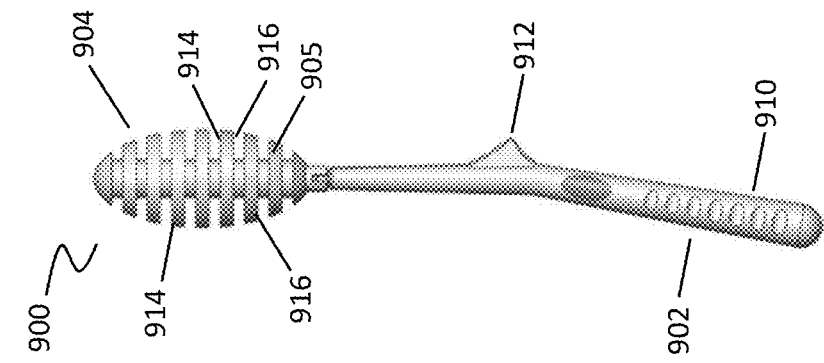

Referring to FIGS. 10A and 10B, an exemplary device for debriding a surface of the vaginal cavity is shown. Device (900) includes a handle (902) and a cleansing tip (904) removably coupled thereto by a ball (906) and socket (908) type connector that may be press fit to join the handle (902) to the cleansing tip (904), and pulled apart to disconnect them from each other. Handle (902) also includes a grip portion (910) and a thumb rest (912). A button (911) may be provided on the handle that may be depressed to actuate dispensing of a substance. The cleansing tip (904) includes a plurality of leaflets (905) having a first set of cleansing surfaces (914) and a second set of cleansing surfaces (916). The leaflets (905) are disposed perpendicular to the axis of the handle so that axial movement in a first direction, e.g., into a body cavity, cleanses the surface of the body cavity with the first set of cleansing surfaces (914), and axial movement in a second opposite direction, e.g., partial or entire withdrawal of the cleansing tip from the body cavity, cleanses the surface of the body cavity with the second set of cleansing surfaces (916). In another variation, as shown in FIGS. 10C to 10F, the vaginal device (918) includes a plurality of leaflets (920) having alternating peaks (922) and troughs (924). The peaks (922) and troughs (924) of each leaflet may be offset as shown in the top view of the device in FIG. 10D to create numerous cleansing surfaces perpendicular to the shaft. Leaflets (925) without peaks and troughs may also be included in the cleansing tip, between leaflets including peaks (922) and troughs (924). In some variations, the peaks and troughs may be aligned and not offset. Furthermore, the height of the peaks may vary between leaflets, as shown in FIG. 10E. The leaflets will generally be sized (e.g., have a diameter, width, height, or thickness) so that they are capable of deforming or folding along the perpendicular axis of the device shaft as the device is moved forward (in direction of arrow A) and backward (in direction of arrow B) within the vaginal cavity, as shown in FIG. 10F. The spacing between the leaflets may also vary and be greater than that shown in FIGS. 10A-10F. Spacing the leaflets further apart may maximize exposure of the leaflet surface area to the surrounding cavity surface.

Substances

In addition to debridement, the devices described herein may deliver one or more substances to the surface of a body cavity. Exemplary classes of substances that may be delivered include, but are not limited to, antiseptic agents, anti-inflammatory agents, anti-allergy agents, fragrances, vaccination substances, or combinations thereof. These may be contained in an emollient base such as, but not limited to, lanolin, aloe vera, vitamin e, glycerin, colloidal silver, zinc derivatives, polysaccharides, propylene glycol, diethylene glycol, triethanolamine, NaOH (sodium hydroxide), or other carriers. Some of these substances may themselves have antibacterial or antiseptic characteristics.

The one or more substances may be included in various types of formulations. For example, the one or more substances may be provided as a liquid, gel, emulsion, or cream formulation. The formulations may be used in combination with the cleansing devices to enhance cleansing of the body cavity surface, for example, by debridement or by reducing the load of infectious agents. The formulation may also be employed to aid movement of the cleansing device within the body cavity so that it glides easier over the cavity surface while rotating or axially translating the device. The enhanced gliding of the device may improve user comfort as it debrides body cavity surfaces. In one variation, gel formulations may be used to aid movement of the cleansing device within the body cavity.

Additionally, gel formulations may be beneficial since they may allow substances such as antiseptic agents to remain in contact with the surface of the body cavity ("dwell time") where micro-organisms are located for a prolonged period of time as opposed to liquid, spray, or powder formulations. The prolonged dwell time may increase the amount of time for the antiseptic agent to work against bacterial or viral contaminants, thereby increasing the efficiency of the disinfecting process. The viscosity of the gel formulations may be adjusted to vary their dwell time, and may range from about 500 cP (0.5 Pa-s) to about 100,000 cP (100 Pa-s), including all values and sub-ranges in between. Viscosity may be adjusted such that the gel formulation has a target dwell time on a body cavity surface that correlates with a kill time for a particular infectious agent. When the gel formulation is to be used in the nasal passages, gel viscosity may range from about 500 cP (0.5 Pa-s) to about 20,000 cP (20 Pa-s), including all values and sub-ranges in between. For example, the viscosity of the gel formulations may be about 500 cP (0.5 Pa-s), about 1,000 cP (1.0 Pa-s), about 2,000 cP (2.0 Pa-s), about 3,000 cP (3.0 Pa-s), about 4,000 cP (4.0 Pa-s), about 5,000 cP (5.0 Pa-s), about 6,000 cP (6.0 Pa-s), about 7,000 cP (7 Pa-s), about 8,000 cP (8.0 Pa-s), about 9,000 cP (9.0 Pa-s), about 10,000 cP (10 Pa-s), about 11,000 cP (11 Pa-s), about 12,000 cP (12 Pa-s), about 13,000 cP (13 Pa-s), about 14,000 cP (14 Pa-s), about 15,000 cP (15 Pa-s), about 16,000 cP (16 Pa-s), about 17,000 cP (17 Pa-s), about 18,000 cP (18 Pa-s), about 19,000 cP (19 Pa-s), or about 20,000 cP (20 Pa-s).

The gels are generally formulated to be clear, but in some variations may be colored. Given that the nasal passages and internal body cavities are sensitive tissues (e.g., they may be mucosal surfaces as opposed to skin, which is generally more robust), the gels may be formulated to address these sensitivities. For example, the gels may be formulated to be hypoallergenic, moisturizing (nondrying), and non-irritating. Maintaining the pH of the gels and other formulations may help minimize irritation in users. In some variations, the pH of the gel formulations described herein may range from about 5.0 to about 8.5. For example, the pH of the gel formulations may be about 5.0, about 5.5, about 6.0, about 6.5, about 7.0, about 7.5, about 8.0, or about 8.5. In other variations, it may be useful for the gel formulations to have a pH ranging from about 7.4 to about 7.7, including all values and sub-ranges in between. For example, it may be useful for the gel formulations to have a pH of about 7.4, about 7.5, about 7.6, or about 7.7. One or more excipients may also be included in the gel formulations that may increase dwell time to kill infectious agents (e.g., bacteria and viruses) and help leave a non-irritating, moisturizing film on the cavity surface.

The antiseptic or antimicrobial agents may include without limitation, antibacterial agents, antiviral agents, antifungal agents, or combinations thereof. Exemplary antiseptic agents that may be suitable for use with the described devices and methods include, but are not limited to, benzalkonium chloride, alcohol, chlorhexidine, iodine, triclosan, colloidal silver solution, herbal solutions, hexylresorcinal and hexachlorophene.

Examples of antibacterial agents that may be suitable for use with the described devices include, but are not limited to, aminoglycosides, amphenicols, ansamycins, betalactams, β-lactams such as penicillins, lincosamides, macrolides, nitrofurans, quinolones, sulfonamides, sulfones, tetracyclines, vancomycin, and any of their derivatives, or combinations thereof. Examples of penicillins that may be suitable for use with the described devices and methods include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin 0, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin.

Examples of antiviral agents suitable for use with the described devices include, but are not limited to, acyclovir, famciclovir, valacyclovir, edoxudine, ganciclovir, foscamet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomethoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxamide), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N,N-bis(2-carbamoylethyl)- sulfonilimino]-1,3,5-triazin-2-ylamino-biphenyl-2-,2'-disulfonic acid disodium salt), BABIM (Bis[5-Amidino-2-benzimidazoly-1]-methane), NIH351, preparations for delivery of vaccines, and combinations thereof.

Examples of antifungal agents suitable for use with the described devices include, but are not limited to, allylamines, imidazoles, polyenes, thiocarbamates, triazoles, and any of their derivatives.

Anti-inflammatory agents may include steroidal and nonsteroidal anti-inflammatory agents. Examples of suitable steroidal anti-inflammatory agents include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

Examples of suitable nonsteroidal anti-inflammatory agents include, but are not limited to, COX inhibitors. These COX inhibitors may include COX-1 or COX nonspecific inhibitors such as, for example, salicylic acid and derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors may also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of anti-allergy agents that may be suitable for use with the described devices include, but are not limited to, pemirolast potassium (ALAMAST®, Santen, Inc.), and any prodrugs, metabolites, analogs, homologues, congeners, derivatives, salts and combinations thereof. An antihistame, a decongestant, a mucolytic agent, or combinations or mixtures thereof may also be delivered to a body cavity surface.

The fragrances or essential oils that may be delivered by the devices described herein in combination with debridement include without limitation, lavender, citrus (e.g. lemon, lime, grapefruit), berry (e.g. raspberry, blackberry, strawberry), rose, mint, *eucalyptus*, cinnamon, and vanilla, or other fruits and/or floral scents, and combinations thereof.

In one variation, a gel formulation may include an antiseptic agent and various other components, for example, one or more excipients. For example, the gel formulation may include benzalkonium chloride as the active antiseptic agent in an amount ranging from about 0.10 w/w % to about 0.15 w/w %. In some variations, the antiseptic gel formulation may include the components listed below in Table 1 and have a viscosity of about 7,420 cP (about 7.4 Pa-s). This antiseptic gel formulation may be beneficial for use in the nose.

TABLE 1

Exemplary Antiseptic Gel Formulation

| Component | w/w % |
| --- | --- |
| Benzalkonium Chloride | 0.13 |
| Carbomer | 0.45 |
| Diethylene Glycol Monoethyl Ether | 10.0 |
| Glycerin | 53.745 |
| Propylene Glycol | 5.0 |
| Triethanolamine | 0.675 |
| Water | 30 |

Excipients that may be included in the gels may form the base of the formulations, and may include, but are not limited to, lanolin, aloe vera, vitamin e, glycerin, colloidal silver, zinc derivatives, polysaccharides, propylene glycol, diethylene glycol, triethanolamine, NaOH (sodium hydroxide), as previously stated. When gel formulations are to be used in the nasal passages, gel viscosity may range from about 500 cP (0.5 Pa-s) to about 20,000 cP (20 Pa-s), including all values and sub-ranges in between. For example, the viscosity of the gel formulation of may be about 500 cP (0.5 Pa-s), about 1,000 cP (1.0 Pa-s), about 2,000 cP (2.0 Pa-s), about 3,000 cP (3.0 Pa-s), about 4,000 cP (4.0 Pa-s), about 5,000 cP (5.0 Pa-s), about 6,000 cP (6.0 Pa-s), about 7,000 cP (7 Pa-s), about 8,000 cP (8.0 Pa-s), about 9,000 cP (9.0 Pa-s), about 10,000 cP (10 Pa-s), about 11,000 cP (11 Pa-s), about 12,000 cP (12 Pa-s), about 13,000 cP (13 Pa-s), about 14,000 cP (14 Pa-s), about 15,000 cP (15 Pa-s), about 16,000 cP (16 Pa-s), about 17,000 cP (17 Pa-s), about 18,000 cP (18 Pa-s), about 19,000 cP (19 Pa-s), or about 20,000 cP (20 Pa-s). In some variations, the viscosity of gels for use in the nasal passages range from about 550 cP (0.55 Pa-s) to about 15,150 cP (1.5 Pa-s.).

The formulations described herein may be effective in killing various infectious agents such as bacteria and viruses. The dwell time of the formulation that may result in over a 99% reduction in the amount of infectious agents present on a cavity surface, and may range from about one minute to about five minutes. In some variations, a dwell time of about one minute may be effective to reduce the load of infectious agents (microbes) by greater than 99%. In other variations, a dwell time of about two minutes may be effective to reduce the load by greater than 99%. In further variations, a dwell time of about five minutes may be effective to reduce the load of infectious agents by greater than 99%. For example, when the gel formulation provided in Table 1 was tested for its time to kill (according to ASTM E2315-16), the percent reduction of the bacteria listed in Table 2 was found to be 99.9% or greater at a dwell time of one minute. Other microbes tested included influenza virus with the percent reduction provided in Table 3. The gel was found to be greater than 99% effective at a dwell time of one minute.

TABLE 2

Percent Reduction of Bacteria At One Minute

| Organism | % Reduction |
| --- | --- |
| *Acinetobacter baumannii* (ATCC 19606) | 99.999 |
| *Bacteroides fragilis* (ATCC 25285) (anaerobic)t | 99.9 |
| *Burkholderia cepacia* (ATCC 25416) | 99.99 |
| *Burkholderia cepacia* (ATCC 25608) | 99.99 |
| *Campylobacter jejuni* (ATTC 33291) (CO2) | 99.99999 |
| *Campylobacter jejuni* (ATTC 49943) (CO2) | 99.99999 |
| *Candida glabrata* (ATCC 2001) | 99.9 |
| *Escherichia coli* (ATCC 25922) | 99.999 |
| *Escherichia coli* (ATCC 11229) | 99.99 |
| *Haemophilus influenza* (CO2) | 99.999 |
| *Klebsiella pneumoniae* (ATCC 13883) | 99.999 |
| *Listeria monocytogenes* (ATCC 7644) | 99.999999 |
| *Micrococcus luteus* (ATCC 7468) | 99.9 |
| *Pseudomonas aeruginosa* (ATCC 27853) | 99.999 |
| *Pseudomonas aeruginosa* (ATCC 15442) | 99.99 |
| *Salmonella enterica* Serovar Enteritidis (ATCC 13076) | 99.999 |
| *Serratia marcescens* (ATCC 8100) | 99.9 |
| *Shigella sonnei* (ATCC 25931) | 99.9999 |
| *Shigella sonnei* (ATCC 9290) | 99.999 |
| *Staphylococcus haemolyticus* (ATCC 29970) | 99.999 |
| *Staphylococcus hominis* (ATCC 27844) | 99.9 |
| *Staphylococcus saprophyticus* (ATCC 15305) | 99.999 |
| *Staphylococcus pneumoniae* (ATCC 49619) (CO2) | 99.999999 |
| *Staphylococcus pneumoniae* (ATCC 6303) (CO2) | 99.999999 |
| *Staphylococcus pyogenes* (ATCC 14289) | 99.9 |

TABLE 3

Percent Reduction of Virus At One Minute

| Organism | % Reduction |
| --- | --- |
| Influenza A (VR-1520) | 99.98 |

At a dwell time of two minutes, the percent reduction of the bacteria listed in Table 4 was found to be 99% or greater with the gel formulation provided in Table 1.

TABLE 4

Percent Reduction of Bacteria At Two Minutes

| Organism | % Reduction |
| --- | --- |
| *Candida albicans* (ATCC 10231) | 99.9 |
| *Enterobacter cloacae* (ATCC 13047) | 99.999999 |
| *Escherichia coli* (ATCC 11775) | 99.9 |
| *Klebsiella pneumoniae* (ATCC 27736) | 99.9 |
| *Listeria monocytogenes* (ATCC 19115) | 99.99 |
| *Salmonella typhimurium* (ATCC 14028) | 99.89 |
| *Staphylococcus epidermidis* (ATCC 12228) | 99.99 |
| *Streptococcus pyogenes* (ATCC 19615) | 99.99 |

At a dwell time of five minutes, the percent reduction of the bacteria listed in Table 5 was found to be 99% or greater with the gel formulation provided in Table 1, except for methicillin resistant *Staphylococcus aureus* (MRSA). At five minutes, a 94.6% reduction was seen for MRSA.

TABLE 5

Percent Reduction of Bacteria At Five Minutes

| Organism | % Reduction |
| --- | --- |
| *Enterococcus faecalis* (ATCC 29212) | 99.999 |
| *Enterococcus faecium* (ATCC 8459) | 99.9 |

TABLE 5-continued

Percent Reduction of Bacteria At Five Minutes

| Organism | % Reduction |
| --- | --- |
| *Enterococcus faecalis* (ATCC 19433) | 99.99 |
| *Proteus mirabilis* (ATCC 12453) | 99.99 |
| *Serratia marcescens* (ATCC 14756) | 99.99999 |
| *Staphylococcus aureus* (ATCC 29213) | 99.99999 |
| *Staphylococcus aureus* (ATCC 6538) | 99.9 |
| Methicillinresistant *Staphylococcus aureus* (ATCC 33592) * | 94.6 |

UV Light

The devices described herein may also include a source of UV light to help sanitize the surface of the body cavity and reduce the load or number of pathogens (e.g., bacteria, viruses, mold, fungi) thereon. The source will typically be a UV-C light source that emits UV light at a wavelength in the range of about 200 nm to about 280 nm. In versions where protection against light exposure to eyes and skin are to be optimized, Far-UVC light in the 207 to 220 nm range may be useful. In one design variation, an optical fiber may be coupled to the UV-C light source in the handle and extend through the interior of the shaft of the device up to the distal end of the cleansing tip. The shaft may be provided with openings in its wall for transmission of the UV-C light therethrough to the body cavity surface. The openings may be disposed in various ways on the shaft. For example, the openings may be provided on the entirety of the shaft, either evenly or unevenly spaced apart on the shaft, or they may be disposed on certain portions of the shaft, or they may form a pattern on the shaft.

Systems

Systems for cleansing a surface of a body cavity are also described herein. In some variations, the systems may be used for debridement. In other variations, the systems may be used to simultaneously cleanse and deposit a substance or formulation onto a body cavity surface.

The systems may include one or more handles and a plurality of cleansing tips. The plurality of cleansing tips may include the same type of tips or different types of tips. In one variation, at least one of the plurality of cleansing tips includes a plurality of leaflets. Other types of cleansing tips, e.g., non-leaflet tips as previously described herein, may be included with the system. Furthermore, when a plurality of handles are included, they may be the same or different. For example, some handles may include a UV light source and/or a cartridge for delivery of a substance to the body cavity surface. In some variations, each handle of a plurality of handles may deliver the same substance or different substances. The handles and tip designs may generally provide an integrated system that allows coupling to be accomplished using a "no touch" technique where the tips are provided in a tray or packaging such that the user does not have to touch the tip in order to attach it to the shaft or handle, but rather the handle can be directly coupled to the tip without physically touching it.

Alternatively, the systems may include one or more cleansing devices and one or more substances. Exemplary classes of substances include, but are not limited to, antiseptic agents, anti-inflammatory agents, anti-allergy agents, fragrances, vaccination substances, or combinations thereof. These may be contained in an emollient base such as, but not limited to, lanolin, aloe vera, vitamin e, glycerin, colloidal silver, zinc derivatives, polysaccharides, propylene glycol, diethylene glycol, triethanolamine, NaOH (sodium hydroxide), or other carriers. The one or more substances may be included in various types of formulations. For example, the one or more substances may be provided as a liquid, gel, emulsion, or cream formulation. When a plurality of cleansing devices are employed, they may have the same cleansing tip or different cleansing tips. For example, the systems may include cleansing devices where all have leaflets disposed parallel to the handle axis or all have leaflets disposed in a helical manner about the handle axis, or where some have leaflets disposed parallel to the handle axis and others have leaflets disposed in a helical manner about the handle axis.

In one variation, the system may include a plurality of cleansing devices and a gel formulation. The gel formulation may comprise an antiseptic agent such as benzalkonium chloride. In addition to reducing the load of infectious agents, the gel formulation once applied to the body cavity surface may aid movement of the cleansing device within the body cavity so that it glides easier over the cavity surface while rotating or axially translating the device. The enhanced gliding of the device may improve user comfort as it debrides the body cavity surface.

When a plurality of leaflets are employed on the cleansing tips, they may include a first set of cleansing surfaces and a second set of cleansing surfaces. The first set of cleansing surfaces may remove debris from the body cavity surface upon movement of the cleansing tip a first direction, and the second set of cleansing surfaces may remove debris or deposit a substance (e.g., an antibacterial or antiviral agent) onto the body cavity surface upon movement of the cleansing tip in a second opposite direction, as previously stated. The first direction and the second opposite direction may rotation, for example, clockwise and counterclockwise rotation, respectively. Alternatively, the first direction and the second opposite direction may be axial translation, for example, back and forth movement into and out of a body cavity. The handles included with the system may be disposable or reusable. The plurality of cleansing tips are generally disposable, but may be configured to be reusable. In some variations, the plurality of leaflets may cleanse when moved in a first direction, and dispense a substance, e.g., an antiviral agent, an antibacterial agent, or an antifungal agent when moved in a second direction. The second direction may be opposite to the first direction.

Figure 13A:
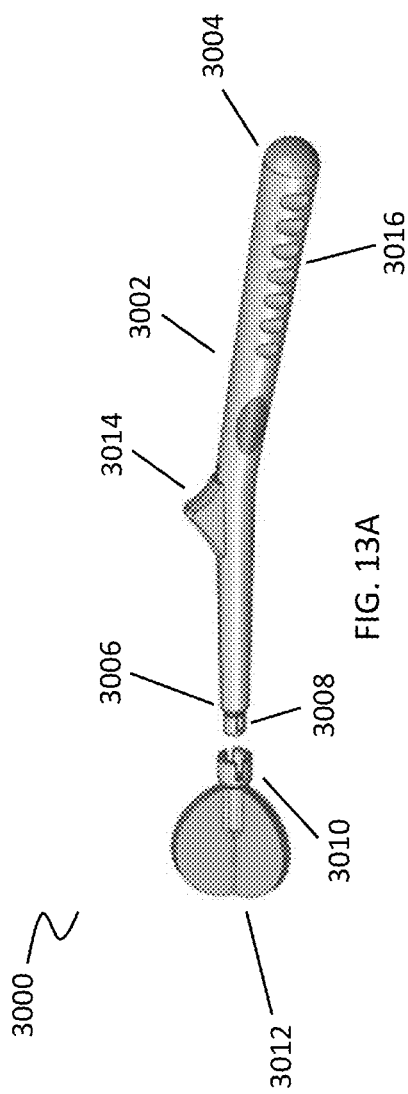
FIGS. 13A and 13B depict an exemplary coupling of the cleansing tip to the handle.
Figure 13B:
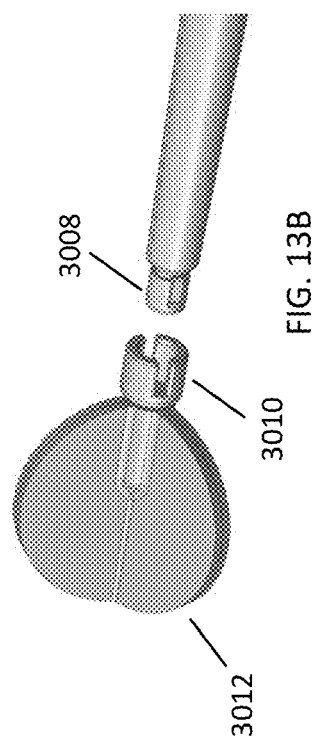
Figure 14:
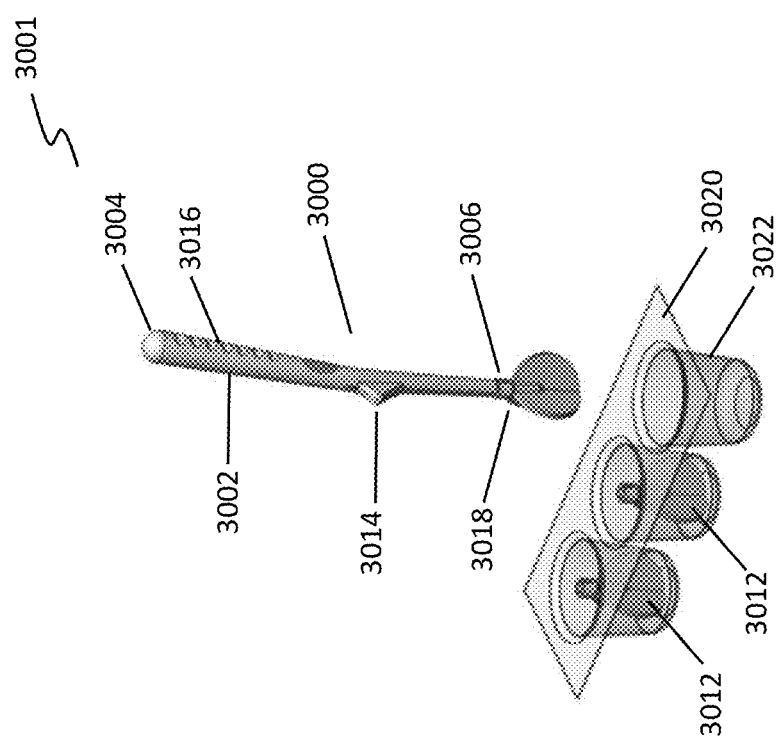
FIG. 14 depicts a system including a handle and a plurality of individually packaged cleansing tips.

In some variations, the systems provide the plurality of cleansing tips in a tray such that they can be coupled to a handle without touching of the tip by the user. In these "no touch" tip systems, the cleansing tips are separated into individual cups or wells formed in the tray. For example, as shown in FIG. 14, the system (3001) includes a tray (3020) comprising one or more cups or wells (3022), where each cup or well (3022) contains a sterile cleansing tip (3012), and one or more handles (3002). When debridement of a body cavity surface is desired, the cleansing tips and a handle are unpackaged, and a debridement device (3000) formed by pressing the distal end (3006) of the handle (3002) onto a cleansing tip (3012) in the cup or well (3022). As shown in FIGS. 13A and 13B, this quick connect mechanism (3018) may comprise a male connector (3008) that is capable of quickly mating with a corresponding female connector (3010) on the cleansing tip (3012). A mechanism for releasing the tip, such as a button on the handle will allow the tip to be dismounted with the "no touch" technique as well, thereby preventing contamination from touching the tip, or contamination of a collected specimen for culture or DNA sampling.

The systems may also be provided as a "kit" where the cleansing tips are packaged in combination with one or more substances. As previously mentioned, the one or more substances may be formulated into a liquid, gel, emulsion, or cream. In one variation, the kit includes a plurality of cleansing tips and one or more packets of a gel formulation. In some variations, the kits include two cleansing tips and one or more packets of a gel formulation. In a further variation, the kits may include two cleansing tips and one packet of an antiseptic gel formulation. The cleansing tips employed may be disposable or reusable. Formulations, including gel formulations, may be placed on the cleansing tip just prior to insertion in a body cavity such as a nasal passage. The kits may be used in the clinical setting, for example, in patients before a surgery or a procedure. They may also be used at home. Other settings include, but are not limited to, nursing homes, restaurants, and other public facilities. The kits may also be provided as sterile or non-sterile.

Methods

Methods for cleansing a surface of a body cavity are further described herein. In general, the methods mechanically debride the body cavity surfaces to reduce the load of particulates or debris on the cavity surfaces. The methods may include inserting a cleansing device into the body cavity, where the cleansing device may comprise a handle and a cleansing tip. Movement of the cleansing tip may then provide the surface area to debride the interior surface of the body cavity, and disperse and/or disrupt micro-organisms such as bacteria, viruses, or biofilms, etc. Movement of the cleansing tip may also enhance spreading of gel formulations, e.g., antiseptic or antibiotic gels, on the body cavity surface.

The cleansing tip may comprise a first set of cleansing surfaces and a second set of cleansing surfaces. Thereafter, the cleansing tip may be moved in a first direction to remove debris from the surface of the body cavity. The texture of the cleansing surfaces may be roughened with bumps, nubs, protrusions, microneedles, barbs, small indentations, and the like, to aid in scraping the body cavity surface to effect debridement. Movement of the cleansing tip in a second opposite direction may further remove debris from the surface of the body cavity. Here, moving the cleansing tip from the first direction to the second opposite direction switches the first set of cleansing surfaces to the second set of cleansing surfaces. In addition, the method may include replacing a used cleansing tip with a new, unused cleansing tip.

Figure 9B:
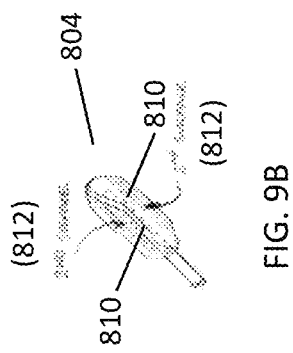
FIGS. 9A-9D illustrate how rotation in opposite directions exposes different sets of cleansing surfaces for debridement of a nasal cavity surface.
Figure 9A:
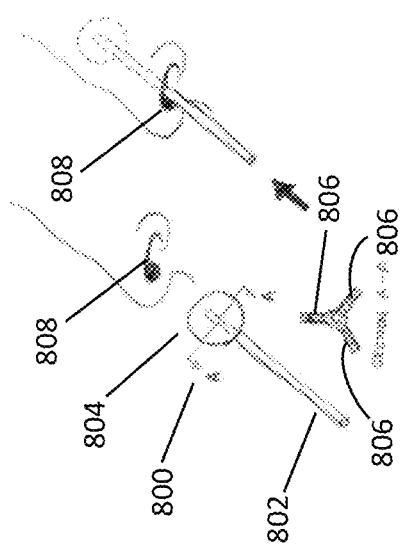
Figure 9D:
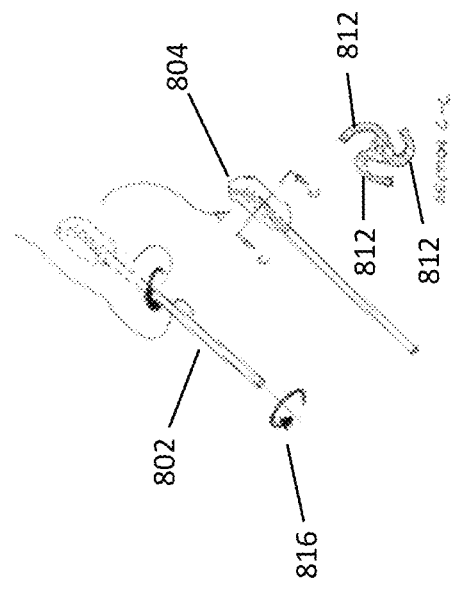
Figure 9C:
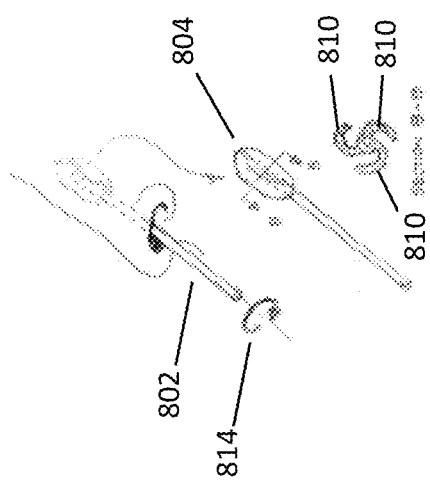

The cleansing tip may be rotated or axially translated to switch the cleansing surfaces from the first set to the second set. As previously described, the cleansing tip may be rotated in a first direction (e.g., clockwise) to cleanse the surface of a body cavity with the first set of cleansing surfaces, and then rotated in a second opposite direction (e.g., counterclockwise) to further cleanse the body cavity surface with the second set of cleansing surfaces. For example, referring to FIGS. 9A and 9B, a debridement device (800) comprising a handle (802) and a cleansing tip (804) may be inserted into the nostril (808) of a user in the direction of the arrow. As shown in the cross-sectional view taken along line A-A, the cleansing tip (804) includes a plurality of leaflets (806). In the side view provided in FIG. 9B, each leaflet (806) of the cleansing tip (804) includes a first set of cleansing surfaces (810) and a second set of cleansing surfaces (812). Debridement of the surface of the nasal cavity may be accomplished by rotating handle (802) clockwise, in the direction of arrow 814, which then rotates the cleansing tip (804) in the clockwise direction. Rotation in the clockwise direction may expose the first set of cleansing surfaces (810), as shown in the cross-sectional view taken along line B-B, such that they contact the nasal cavity surface and debride the surface. Further debridement may be performed by rotating the handle (802) in the opposite direction, i.e., counterclockwise, in the direction of arrow (816), which then rotates the cleansing tip (804) in the counterclockwise direction. Rotation in the counterclockwise direction may expose the second set of cleansing surfaces (812), as shown in the cross-sectional view taken along line C-C, such that they contact the nasal cavity surface to further debride the surface.

Similarly, the cleansing tip may be axially translated in a first direction (e.g., advanced into a body cavity) to cleanse the surface of a body cavity with the first of cleansing surfaces, and then axially translated in a second opposite direction (e.g., withdrawn from the body cavity) to further cleanse the surface of the body cavity with the second set of cleansing surfaces. Axial translation may be useful when the surface of the vaginal cavity is to be debrided. For example, referring to FIGS. 10A and 10B, an exemplary device for debriding a surface of the vaginal cavity is shown. Device (900) includes a handle (902) and a cleansing tip (904) removably coupled thereto by a ball (906) and socket (908) type connector that may be press fit to join the handle (902) to the cleansing tip (904), and pulled apart to disconnect them from each other. Handle (902) also includes a grip portion (910) and a thumb rest (912). The cleansing tip (904) includes a plurality of leaflets (905) having a first set of cleansing surfaces (914) and a second set of cleansing surfaces (916). The leaflets (905) are disposed perpendicular to the axis of the handle so that axial movement in a first direction, e.g., into a body cavity, cleanses the surface of the body cavity with the first set of cleansing surfaces (914), and axial movement in a second opposite direction, e.g., partial or entire withdrawal of the cleansing tip from the body cavity, cleanses the surface of the body cavity with the second set of cleansing surfaces (916).

Figure 12C:
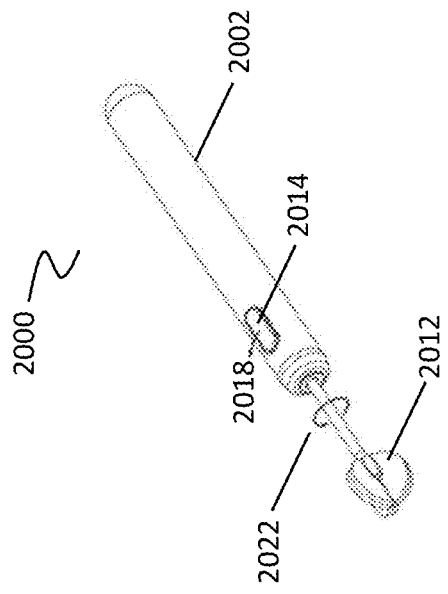
Figure 12B:
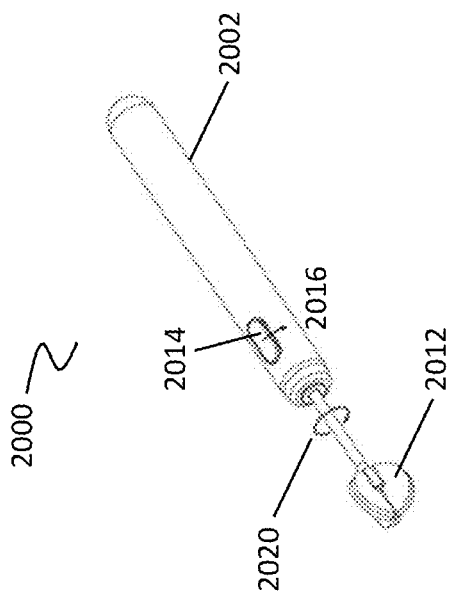

Movement of the cleansing tip may be manual, for example, by rotating or axially translating the handle of the device by hand. Alternatively, movement of the cleansing tip may be automated, for example, via actuation by a motor housed within the handle. For example, as shown in FIGS. 12B and 12C, the debridement device (2000) may include a toggle or switch (2014) on the handle (2002) to actuate motorized rotation of the cleansing tip (2012). When the switch (2014) is shifted in the direction of arrow (2016), the motor (not shown) within the handle (2002) rotates the cleansing tip (2012) clockwise, in the direction of arrow (2020). When rotation in the opposite direction is desired, switch (2014) may be shifted in the direction of arrow (2018) so that the motor (not shown) within the handle (2002) rotates the cleansing tip (2012) counterclockwise, in the direction of arrow (2022).

Various body cavity surfaces may be debrided with the cleansing devices described herein. For example, surfaces such as the skin and hair region of the nostrils, and inside the nasal cavity, the oral cavity, the ear canal, or the vaginal cavity may be debrided. Particulates or debris that may be removed include without limitation, mucus, dust, pollen, dead skin cells, bacteria, viruses, and combinations thereof. Given that particulate or debris are being captured and removed by the cleansing tips, they may also be used as swabs for collecting samples. The samples may be collected for bacterial or viral cultures or for DNA analysis of cells. Other uses for the samples are also contemplated.

In addition to debridement, the devices may also deliver a substance to the surface of the body cavity. Exemplary classes of substances that may be delivered include, but are not limited to, antiseptic agents, anti-inflammatory agents, anti-allergy agents, fragrances, or combinations thereof. The antiseptic agents may include antibacterial agents, antiviral agents, or combinations thereof. The substance may be delivered prior to debridement, during debridement, and/or after debridement. Furthermore, the substances may be provided in a liquid, gel, emulsion, or cream formulation. The devices may also be used to dispense other therapeutic substances such as vaccinations.

The antiseptic agents may include antibacterial agents, antiviral agents, antifungal agents, or combinations thereof. Exemplary antiseptic agents that may be suitable for use with the described methods include, but are not limited to, alcohol, chlorhexidine, iodine, triclosan, and hexachlorophene, hydrogen peroxide.

Examples of antibacterial agents that may be suitable for use with the described methods include, but are not limited to, aminoglycosides, amphenicols, ansamycins, betalactams, β-lactams such as penicillins, lincosamides, macrolides, nitrofurans, quinolones, sulfonamides, sulfones, tetracyclines, vancomycin, and any of their derivatives, or combinations thereof. Examples of penicillins that may be suitable for use with the described devices and methods include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin.

Examples of antiviral agents suitable for use with the described methods include, but are not limited to, acyclovir, famciclovir, valacyclovir, edoxudine, ganciclovir, foscamet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomet-hoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxamide), LY253963 (1,3,4-thiadiazol-2-yl-cyanamide), RD3-0028 (1,4-dihydro-2,3-Benzodithiin), CL387626 (4,4'-bis[4, 6-d][3-aminophenyl-N,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazoly-1]-methane), NIH351, and combinations thereof.

Examples of antifungal agents suitable for use with the described methods include, but are not limited to, allylamines, imidazoles, polyenes, thiocarbamates, triazoles, and any of their derivatives.

Anti-inflammatory agents may include steroidal and non-steroidal anti-inflammatory agents. Examples of suitable steroidal anti-inflammatory include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethyl-amino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

Examples of suitable nonsteroidal anti-inflammatory agents include, but are not limited to, COX inhibitors. These COX inhibitors may include COX-1 or COX nonspecific inhibitors such as, for example, salicylic acid and derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors may also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of anti-allergy agents that may suitable for use with the described methods include, but are not limited to, pemirolast potassium (ALAMAST®, Santen, Inc.), and any prodrugs, metabolites, analogs, homologues, congeners, derivatives, salts and combinations thereof. An antihistame, a decongestant, a mucolytic agent, or combinations or mixtures thereof may also be delivered to a body cavity surface.

The fragrances or essential oils that may be delivered by the methods described herein include without limitation, lavender, citrus (e.g. lemon, lime, grapefruit), berry (e.g. raspberry, blackberry, strawberry), rose, mint, eucalyptus, cinnamon, vanilla, and combinations of these with other scents or emollients or other carriers or thickeners to achieve the proper consistency.

The cleansing devices and systems may be used in various ways. In some variations, the devices and systems may be used to cleanse a body cavity surface prior to, after, or both prior to and after, a surgery or a medical procedure, visiting a nursing home, visiting a hospital, attending a social gathering, traveling, or going to a public space. Alternatively, the cleansing may be performed as frequently as desired, for example, once a day, twice a day, three times a day, etc In some instances, cleansing may be performed every four to six hours. A substance or formulation, e.g., an antiseptic gel formulation, may be delivered during one or more periods of cleansing.

The subjects that may use the devices and systems may include, but not be limited to, a medical patient, a healthcare worker, a first responder, a food service worker, an immunocompromised subject, or a nursing home resident. In some instances, the user may be an individual that is part of the general public.

Additionally, or alternatively, the device may emit UV light to help sanitize the surface of the body cavity and reduce the load or number of pathogens (e.g., bacteria, viruses, mold, fungi) thereon. The source will typically be a UV-C light source that emits UV light at a wavelength in the range of about 200 nm to about 280 nm.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated.

The invention claimed is:

1. A device for cleansing a surface of a body cavity comprising:
   a handle comprising a proximal end and a distal end, defining a longitudinal axis; and
   a molded elastomer cleansing tip disposed at the distal end, the cleansing tip comprising a plurality of flexible leaflets disposed helically with respect to the longitudinal axis,
   wherein each leaflet of the plurality of flexible leaflets comprises a first cleansing surface and a second cleansing surface on the opposite side of the first cleansing surface, and wherein upon rotation of the cleansing tip, each leaflet of the plurality of leaflets flips to expose only one cleansing surface to the body cavity surface at a time, the first cleansing surface exposed to the body cavity surface upon rotation of the cleansing tip in a first direction; and the second cleansing surface exposed to the body cavity surface-upon rotation of the cleansing tip in a second opposite direction, and wherein the first cleansing surface and the second cleansing surface are symmetrical.

2. The device of claim 1, wherein the first and second cleansing surfaces are configured to remove mucus, dust, pollen, dead skin cells, bacteria, bacterial biofilms, viruses, or combinations thereof from the body cavity surface.

3. The device of claim 1, wherein the cleansing tip comprises three leaflets.

4. The device of claim 1, wherein the cleansing tip is disposable or reusable.

5. The device of claim 1, wherein the cleansing tip has a collapsed configuration.

6. A method for cleansing a surface of a body cavity comprising:
   inserting a cleansing device into the body cavity of a user, the cleansing device comprising:
      a handle comprising a proximal end and a distal end, defining a longitudinal axis; and
      a molded elastomer cleansing tip, the cleansing tip comprising a plurality of flexible leaflets disposed helically with respect to the longitudinal axis, wherein each leaflet of the plurality of flexible leaflets comprises a first cleansing surface and a second cleansing surface on the opposite side of the first cleansing surface, and wherein upon rotation of the cleansing tip, each leaflet of the plurality of leaflets flips to expose only one cleansing surface to the body cavity surface at a time, the first cleansing surface exposed to the body cavity surface upon rotation of the cleansing tip in a first direction, and the second cleansing surface exposed to the body cavity surface upon rotation of the cleansing tip in a second opposite direction, and wherein the first cleansing surface and the second cleansing surface are symmetrical;

rotating the cleansing tip in the first direction; and optionally rotating the cleansing tip in the second opposite direction.

7. The method of claim 6, wherein the body cavity is a nasal cavity.

8. The method of claim 7, wherein the nasal cavity comprises skin and hair of a nostril.

9. The method of claim 8, further comprising removing the hair from the nostril.

10. The method of claim 6, wherein the first and second cleansing surfaces are configured to remove mucus, dust, pollen, dead skin cells, bacteria, bacterial biofilms, viruses, or combinations thereof from the body cavity surface.

11. The method of claim 6, further comprising applying a gel formulation to the cleansing tip and distributing the gel formulation to the surface of the body cavity when rotating the cleansing tip between the first direction and second opposite direction.

12. The method of claim 11, wherein the gel formulation comprises an antiseptic agent.

13. The method of claim 11, wherein the gel formulation has a viscosity ranging from about 500 cP (0.5 Pa-s) to about 20,000 cP (20 Pa-s).

14. The method of claim 13, further comprising adjusting the viscosity such that the gel formulation has a dwell time on the body cavity surface that correlates with a kill time for an infectious agent.

15. The method of claim 6, wherein cleansing is performed prior to, after, or both prior to and after, a surgery or a medical procedure, visiting a nursing home, visiting a hospital, attending a social gathering, traveling, or going to a public space.

16. The method of claim 6, wherein the plurality of leaflets are configured to conform to the shape of the body cavity.

17. The method of claim 6, further comprising adjusting the amount of force applied to the cleansing tip depending on the body surface to be cleansed.

18. A system for cleansing a surface of a body cavity comprising:

one or more cleansing devices, each of the one or more cleansing devices comprising a handle comprising a proximal end and a distal end, defining a longitudinal axis, and a molded elastomer cleansing tip, wherein each molded cleansing tip comprises a plurality of flexible leaflets disposed helically about the longitudinal axis, and wherein each leaflet of the plurality of flexible leaflets comprises a first cleansing surface and a second cleansing surface on the opposite side of the first cleansing surface, and wherein upon rotation of the cleansing tip, each leaflet of the plurality of leaflets flips to expose only one cleansing surface to the body cavity surface at a time, the first cleansing surface exposed to the body cavity surface upon rotation of the cleansing tip in a first direction, and the second cleansing surface exposed to the body cavity surface-upon rotation of the cleansing tip in a second opposite direction, and wherein the first cleansing surface and the second cleansing surface are symmetrical; and one or more gel formulations comprising an active agent.

19. The system of claim 18, wherein the body cavity is a nasal cavity.

20. The system of claim 18, wherein the first and second cleansing surfaces are configured to remove mucus, dust, pollen, dead skin cells, bacteria, bacterial biofilms, viruses, or combinations thereof from the body cavity surface.

21. The system of claim 18, wherein the one or more gel formulations comprises an antiseptic agent.

22. The system of claim 21, wherein the active agent comprises benzalkonium chloride.

23. The system of claim 18, wherein the one or more gel formulations comprises an essential oil of mint.

* * * * *